(12) United States Patent
Snyder et al.

(10) Patent No.: US 6,936,243 B2
(45) Date of Patent: Aug. 30, 2005

(54) ADENO-ASSOCIATED VIRAL VECTOR-MEDIATED DELIVERY OF DNA TO CELLS OF THE LIVER

(75) Inventors: Richard O. Snyder, Oakland, CA (US); Lawrence K. Cohen, Oakland, CA (US); Mark A. Kay, Seattle, WA (US); Olivier Danos, Fontainebleau (FR); Arthur R. Thompson, Seattle, WA (US)

(73) Assignees: The University of Washington, Seattle, WA (US); Cell Genesys, Inc., Foster City, CA (US)

( * ) Notice: Subject to any disclaimer, the term of this patent is extended or adjusted under 35 U.S.C. 154(b) by 0 days.

(21) Appl. No.: 09/576,858

(22) Filed: May 22, 2000

(65) Prior Publication Data

US 2002/0151509 A1 Oct. 17, 2002

Related U.S. Application Data

(63) Continuation of application No. 08/882,044, filed on Jun. 25, 1997, now abandoned.
(60) Provisional application No. 60/032,506, filed on Dec. 2, 1996.

(51) Int. Cl.⁷ ................ A61K 48/00; C12N 15/864
(52) U.S. Cl. ............... 424/93.2; 514/44; 435/455; 435/456; 435/320.1
(58) Field of Search .............. 424/93.2; 514/44; 435/455, 456, 457, 320.1

(56) References Cited

U.S. PATENT DOCUMENTS

| | | | |
|---|---|---|---|
| 5,139,941 A | 8/1992 | Muzyczka et al. | 435/456 |
| 5,693,531 A | 12/1997 | Chiorini et al. | 435/325 |
| 5,756,283 A | 5/1998 | Wilson et al. | 435/5 |
| 6,268,213 B1 | 7/2001 | Samulski et al. | 435/320.1 |
| 2001/0051611 A1 * | 12/2001 | Srivastava et al. | 514/44 |

FOREIGN PATENT DOCUMENTS

WO    WO 9809524    12/1998

OTHER PUBLICATIONS

Chuah et al., "Gene Therapy for Hemophilia", J of Gene Medicine 3:3–20, 2001.
Wang et al., "Sustained Expression . . . in Liver", Mol Ther. 1:154–158, 2000.
Chao et al., "Sustained Expression . . . a Parvovirus–based Vector", Blood 95:1594–1599, 2000.
Kay et al., "Evidence for . . . with an AAV Vector", Nat Genet 24:257–261, 2000.
Koeberl et al., "Persistent. Therapeutically . . . Virus Vectors", Hum Gene Ther 10:2133–2140, 1999.
Liu et al., "Transduction . . . virus", J Interf Cytokine Res 1:21–30, 2000 (Abstract).
*Gene Therapy* (1995) 2, 29–37, Flotte et al. "An improved system for packaging recombinant adeno–associated virus vectors capable of in vivo transduction."
*Human Gene Therapy*, vol. 5, pp. 793–801 (1994). Kotin, "Prospects for the Use of Aden–Associated Virus as a Vector for Human Gene Therapy."
Orkin et al. "Report and Recommendations of the Panel to Assess the NIH Investment in Research on Gene Therapy", issued by the U.S. National Institutes of Health. (1995).
*Journal of Virology.* vol. 70, No. 1, pp. 520–532 (1996).

(Continued)

Primary Examiner—Scott D. Priebe
(74) Attorney, Agent, or Firm—Piper Rudnick LLP; Steven B. Kelber; Linda R. Judge

(57) ABSTRACT

The instant invention provides methods of expressing polynucleotides in the cells of the liver comprising administering viral particles comprising a recombinant AAV vector into a mammal, preferably a human.

5 Claims, 11 Drawing Sheets

OTHER PUBLICATIONS

Fisher et al. "Transduction with Recombinant Adeno–Associated Virus for Gene Therapy is Limited by Leading–Strand Synthesis."
*Human Gene Therapy.* vol. 8, pp. 125–135 (1997). Chen et al. "Comparison of Retroviral and Adeno–Associated Viral Vectors Designed to Express Human Clotting Factor IX."
*Cas. Lek. Ces.* vol. 134, No. 19, pp. 625–629 (1995), Sokol and Prchal "Human Genome—Chromsome No. 19".
*Human Gene Therapy.* vol. 7, pp. 463–470 (1996), Su et al. Selective Killing of AFP–Positive Hepatocellular Carcinoma Cells by Adeno–Associated Virus Transfer of the Herpes Simplex Virus Thymidine Kinase Gene.
*Journal of Virology.* vol. 70, No. 3, pp. 1668–1677 (1996). Wang et al. "Rescue and Replication of Adeno–Associated Virus Type 2 as well as Vector DNA Sequences from Recombinant Plasmids Containing Deletions in the Viral Inverted Terminal Repeats: Selective Encapsidation of Viral Genomes in Progeny Virions."
*Journal of Molecular Biology.* vol. 250, pp. 573–580 (1995). Wang et al. "Rescue and Replication Signals of the Adeno–Associated Virus 2 Genome."

*Blood.* vol. 86(10 Suppl. 1): p. 240a (1995) Ponnazhagen et al. "Adeno–Associated Virus 2–Mediated Gene Transfer and Expression in Murine Hematopoietic Progenitor Cells."

*Proc. Natl. Acad. Sci. USA.* vol. 94, pp. 1426–1431 (1997) Koeberl et al. "Persistent Expression of Human Clotting Factor IX from Mouse Liver after Intravenous Injection of Adeno–Associated Virus Vecotrs."

*Am. J. of Human Genetics.* vol. 57, Suppl. 4, p. A43 (1995) Koeberl et al. "Transduction of Hepatocytes in vivo with Adeno–Associated Virus Vectors as a Model for Hepatic Gene Therapy."

*Human Gene Therapy.* vol. 7 pp. 1781–1790 (1996) Ross et al. "Gene Therapy in the United States: A Five Year Status Report."

*Proc. Natl. Acad. Sci.* vol. 91 pp. 8915–8919 Russell et al. "Adeno–associated virus vectors preferentially transduce cells in S phase."

* cited by examiner rAAV Production

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO: 1:

ACTCCATCAC TAGGGGTTCC                    20

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 2:

GGTAATGATT AACCCGCCAT GCTACTTATC                                30

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 3:

TCAGAATCTG GCGGCAACTC CC                                        22

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 4:

TCGTCAAAAA GGCGTATCAG                                            20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 5:

TCCCTTGTCG AGTCCGTTGA                                            20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 6:

CAGAAGGAAA ACAGCAAACG                                            20

-continued (2) INFORMATION FOR SEQ ID NO: 7:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
AGAGGGAGTG GCCAACTCCA TCACTAGGGG TTCCTGGAGG GGTGGAGTCG TGACGTGAAT        60

TACGTCATAG GGTTAGGGAG GTCC                                              84
```

(2) INFORMATION FOR SEQ ID NO: 8:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "recombinant"

(xi) SEQUENCE DESCRIPTION: SEQ ID NO: 8:

```
AGAGGGAGTG GCCAACTCCA TCACTAGGGG TTCCTTGTAG TTAATGATTA ACCCGCCATG        60

CTACTTATCT ACGTAGCCAT GCTCTAGA                                          88
```

ADENO-ASSOCIATED VIRAL VECTOR-MEDIATED DELIVERY OF DNA TO CELLS OF THE LIVER

The instant application is a continuation of U.S. Ser. No. 08/882,044 filed 25 Jun. 1997. abandoned, which claims benefit to U.S. Ser. No. 60/032,506 filed 2 Dec. 1996. +gi

ACKNOWLEDGEMENTS

The invention disclosed in the instant application was supported in part by NIH grant HL53682. The U.S. Government may have rights in certain portions of the invention disclosed herein.

INTRODUCTION

BACKGROUND

The first human gene therapy trial started in September of 1990 and involved retrovirally-mediated transfer of the adenosine deaminase (ADA) gene into lymphocytes of patients with severe combined immunodeficiency (SCID). The favorable results of that trial stimulated further interest in gene therapy resulting in additional gene therapy clinical protocols approved by the NIH Recombinant DNA Advisory Committee (RAC). Although the original promise of gene therapy was the development of a curative treatment for simple, single gene diseases, the vast majority of gene therapy trials were directed to complex genetic or acquired diseases, such as cancer and infectious disease. A large number of the initial clinical gene transfer studies were not gene therapy per se but rather gene marking studies. The first type of marking experiments used tumor infiltrating lymphocytes which were transduced in vitro with retroviral vectors prior to infusion into patients with cancer. The second class of gene marking studies involved the attempt to detect residual tumor cells in marrow infused into patients following ablative chemotherapy.

Of the currently approved gene therapy trials, all trials prior to 1992 used retroviral vectors and the diseases targeted included SCID, familial hypercholesteremia and cancer. More recently, gene therapy trials have commenced for AIDS and Hemophilia B, again using retroviral vectors.

In addition, adenoviral and AAV vectors have recently been approved for cystic fibrosis. The available data appears promising, for example the expression of the LDL receptor in the liver following ex vivo transduction of resected hepatocytes and infusion into the portal vein in patients with familial hypercholesteremia resulted in a 20% drop in plasma cholesterol levels (see e.g., Grossman et al., Nature Genetics, 6:335–341 (1994)). It is likely therefore that there will be an exponential growth in gene therapy trials and a large number of medical schools and teaching hospitals are setting up gene therapy centers.

One goal of gene therapy is to provide long-term, therapeutically effective levels of expression of a particular gene of interest in or adjacent to the tissues where such gene expression is therapeutically beneficial. That goal requires, for example, expression of the gene of interest in the targeted tissues, which requires, in the case of AAV vectors, at least a promoter in the recombinant AAV vector that operates in the targeted tissues, and a mode of administration that delivers the recombinant AAV vector to the appropriate tissues.

HERPES VIRUSES

The genome of the herpes simplex virus type-1 (HSV-1) is about 150 kb of linear, double-stranded DNA, featuring about 70 genes. Many viral genes may be deleted without the virus losing the ability to propagate. The "immediate early" (IE) genes are transcribed first. They encode trans-acting factors which regulate expression of other viral genes. The "early" (E) gene products participate in replication of viral DNA. The late genes encode the structural components of the virion as well as proteins which turn on transcription of the IE and E genes or disrupt host cell protein translation.

After viral entry into the nucleus of a neuron, the viral DNA can enter a state of latency, existing as circular episomal elements in the nucleus. While in the latent state, transcriptional activity is reduced. If the virus does not enter latency, or if reactivated, the virus produces numerous infectious particles, which leads rapidly to the death of the neuron. HSV-1 is transported efficiently between synaptically connected neurons and hence, can spread rapidly through the nervous system.

Two types of HSV vectors have been utilized for gene transfer into the nervous system. Recombinant HSV vectors involve the removal of an immediate-early gene within the HSV genome (ICP4, for example), and replacement thereof with the gene of interest. Although removal of this gene prevents replication and spread of the virus within cells which do not complement for the missing HSV protein, all of the other genes within the HSV genome are retained. Replication and spread of such viruses in vivo therefore is limited, but expression of viral genes within infected cells continues.

Several of the viral expression products may be toxic to the recipient cell and expression of viral genes within cells expressing MHC antigens can induce harmful immune reactions. In addition, nearly all adults harbor latent herpes simplex virus within neurons and the presence of recombinant HSV vectors could result in recombination which can produce an actively replicating wild-type virus. Alternatively, expression of viral genes from the recombinant vector within a cell harboring a latent virus might promote reactivation of the virus. Finally, long-term expression from the recombinant HSV vector has not been demonstrated reliably. It is likely that except for conditions in which latency is induced, the inability of HSV genomes to integrate within host DNA results in susceptibility to degradation of the vector DNA.

In an attempt to circumvent the difficulties inherent in the recombinant HSV vector, defective HSV vectors were employed as gene transfer vehicles within the nervous system. The defective HSV vector is a plasmid-based system whereby a plasmid vector (termed an amplicon) is generated which contains the gene of interest and two cis-acting HSV recognition signals which are the origin of DNA replication and the cleavage packaging signal. In the presence of HSV proteins provided by a helper virus, the amplicon is replicated and packaged. The vector therefore expresses no viral gene products within the recipient cell and recombination with or reactivation of latent viruses by the vector is limited due to the minimal amount of HSV DNA sequence present within the defective HSV vector genome. The major limitation of that system, however, is the inability to eliminate residual helper virus from the defective vector stock. The helper virus is often a mutant HSV which, like the recombinant vectors, can replicate only under permissive conditions in tissue culture. The continued presence of mutant helper HSV within the defective vector stock, however, presents problems which are similar to those enumerated above in regard to the recombinant HSV vector.

ADENOVIRUSES

The adenovirus genome consists of about 36 kb of double-stranded DNA. Adenoviruses target airway epithelial cells but are capable of infecting other cells.

Recombinant adenovirus vectors have been used as gene transfer vehicles for non-dividing cells. The vectors are similar to recombinant HSV vectors, since the adenovirus E1a immediate-early gene is removed but most viral genes are retained. Since the E1a gene is small (roughly 1.5 kb) and the adenovirus genome is ⅓ the size of the HSV genome, other non-essential adenovirus genes are removed in order to insert a foreign gene within the adenovirus genome.

In nature, diseases resulting from adenovirus infections are not as severe as those induced by HSV infection. That is the principal advantage of recombinant adenovirus vectors as compared with HSV vectors. However, retention and expression of many adenovirus genes presents problems similar to those described with the HSV vector, particularly the problem of cytotoxicity to the recipient cell. In addition, recombinant adenovirus vectors often elicit immune responses which may serve to limit the effectiveness of vector-mediated gene transfer and may provide another means for destruction of transduced cells. Finally, as with the HSV vectors, stability of long-term expression is unclear since there is no mechanism for high frequency specific viral integration in the genome of non-dividing host cells. While theoretically possible, defective adenovirus vectors would be difficult to make as at least 20% of the Ad genome is required for packaging (about 27 Kb) and vectors of that size are difficult to work with.

ADENO-ASSOCIATED VIRUS

Adeno-associated virus (AAV) is a defective parvovirus whose genome is encapsidated as a single-stranded DNA molecule. Strands of plus and minus polarity are packaged with equal efficiency, but in separate virus particles. Although AAV can replicate under special circumstances in the absence of a helper virus, efficient replication requires coinfection with a helper virus of the herpesvirus or adenovirus family. In the absence of the helper virus, AAV establishes a latent infection in which the viral genome exists as an integrated provirus in the host cell. The integration of the virus is site-specific (human chromosome 19). If a latently infected cell line later is superinfected with a suitable helper virus, the AAV provirus is excised and the virus enters the "productive" phase. However, it has been reported that some AAV-derived transducing vectors are not rescued by adenovirus superinfection.

AAV isolates have been obtained from human and simian clinical specimens. The host range for lytic growth of AAV is unusually broad. Cell lines from virtually every mammalian species tested (including a variety of human, simian, canine, bovine and rodent cell lines) can be infected productively with AAV, provided an appropriate helper virus is used (e.g., canine adenovirus in canine cells). However, no disease has been associated with AAV in either human or other animal populations.

AAV has been isolated as a nonpathogenic coinfecting agent from fecal, ocular and respiratory specimens during acute adenovirus infections, but not during other illnesses. Latent AAV infections have been identified in both human and nonhuman cells. Overall, virus integration appears to have no apparent effect on cell growth or morphology, see Samulski, Curr. Op. Gen. Devel., 3:74–80 (1993).

There are a number of AAV's, including AAV-1, AAV-2, AAV-3, AAV-4 and AAV-5. The genome of AAV-2 is 4,675 bases in length and contains inverted terminal repeat sequences of 145 bases each. These repeats are believed to act as origins for DNA replication. The AAV-3 genome is 4726 bases in length and has 82% overall sequence homology with AAV-2, see S. Muramatsu, Virology, 221:208–217 (1996). Like AAV-2, both ends of the AAV-3 genome consist of inverted repeats containing 146 bp palindromes. Also the nonstructural Rep protein binding motif and terminal resolution site in the hairpin is highly conserved, with only a single base-pair substitution between AAV-2 and AAV-3.

The AAV genome has two major open reading frames. The left frame encodes at least four non-structural proteins (the Rep group). There are two promoters P5 and P19, which control expression of those proteins. As a result of differential splicing, the P5 promoter directs production of proteins Rep 78 and Rep 68, and the P19 promoter, Rep 52 and Rep 40. The Rep proteins are believed to be involved in viral DNA replication, trans-activation of transcription from the viral promoters, repression of heterologous enhancers and promoters, and site-specific integration.

The right ORF, controlled by the P40 promoter, encodes the capsid proteins Vp1 (91 kDa), Vp2 (72 kDa) and Vp3 (60 kDa). Vp3 comprises 80% of the virion structure, while Vp1 and Vp2 are minor components. There is a polyadenylation site at map unit 95. For the complete sequence of the AAV-2 genome, see Strivastava et al., J. Virol., 45:555–64 (1983).

McLaughlin et al., J. Virol., 62:1963–73 (1988) prepared two AAV vectors: dl 52–91, which retains the AAV rep genes, and dl 3–94, in which all of the AAV coding sequences have been deleted. dl 3–94 does, however, retain the two 145 base terminal repeats, and an additional 139 bases which contain the AAV polyadenylation signal. A foreign gene, encoding neomycin resistance, was inserted into the vector. Viral stocks were prepared by complementation with a recombinant AAV genome, which supplied the missing AAV gene products in trans but was itself too large to be packaged. Unfortunately, the virus stocks were contaminated with wild type AAV (10% in the case of dl 3–94) presumably as a result of homologous recombination between the defective and the complementing viruses.

Samulski et al., J. Virol., 63:3822–28 (1989) developed a method of producing recombinant AAV stocks without detectable wild-type helper AAV. The AAV vector retained only the terminal 191 bases of the AAV chromosome. In the AAV helper plasmid (pAAV/Ad), the terminal 191 bases of the AAV chromosome were replaced with adenovirus terminal sequences. Since sequence homology between the vector and the helper AAV thus essentially was eliminated, no detectable wild-type AAV was generated by homologous recombination. Moreover, the helper DNA itself was not replicated and encapsidated because the AAV termini are required for that process. Thus, in the AAV system, unlike the HSV system, helper virus could be eliminated completely leaving a helper-free AAV vector stock.

Recombinant AAV (rAAV) vectors have been used as vectors for expressing gene products in animals, see, for example, U.S. Pat. No. 5,193,941 and WO 94/13788. A number of patents and other publications describe numerous AAV vectors and uses, the uses generally being related to expression of gene products either in vitro (usually tissue cultures) or in vivo (usually in the lungs or oral mucosa, the normal sites of AAV infection, although expression in the central nervous system and in cardiac tissue has been found).

Transductions carried out by single injection into the quadriceps of mice using rAAV vectors harboring the bacterial β-galactosidase gene demonstrated that expression can be maintained long-term and the expression does not decrease substantially during that time (Xiao et al., J.Virol., 70:8098–8108 (1996). Other targets successfully transduced with rAAV vectors include: T-lymphocytes and B-lymphocytes (Muro-Cacho et al., J. Immunother., 11:231–237 (1992)), human erythroleukemia cells (Walsh et al., Proc. Nat. Acad. Sci. USA, 89:7257–61 (1992)), different regions of the rat brain (McCown et al. (1996)), the striatum of the rat brain in a Parkinson's Disease Model with the tyrosine hydroxylase gene (Kaplitt et al. (1994)), heart of the pig and rat with the LacZ gene (Kaplitt et al., Ann. Thoracic Surg., 62:1669–1676 (1996)), the peripheral auditory system of the guinea pig (Lalwani et al. (1996)) and bronchial epithelia of the rabbit and monkey (Flotte et al. (1993); Afione et al. (1996)). In addition, a Phase I human clinical trial for the delivery of an rAAV-CFTR vector is in progress (Flotte et al. (1996)).

Attempts made to develop effective gene therapy for expressing exogenous DNA from the liver include in vivo and ex vivo methods using recombinant retroviruses (Kay et al., Hum. Gen. Ther., 3:641–647; Kay et al., Proc. Natl. Acad. Sci. USA, 89:89–93), recombinant adenoviruses (Walter et al., Proc. Natl. Acad. Sci. USA, 93:3056–3061; Li et al., Hum. Gen. Ther., 4:403–409) and recombinant herpesviruses (Miyanohara et al., New Biol., 4:238–242). In addition, a person with familial hypercholesterolemia was treated ex vivo with a recombinant retrovirus expressing the LDL receptor (Grossman et al., Nature Genet., 6:335–341 (1994)). However, those attempts did not involve use of an rAAV vector.

The liver is the target of a number of different viral infections and other disorders. For example, Hepatitis B Virus, a virus distinct from AAV, may result in liver infections ranging from subclinical infections to acute hepatitis, eventually leading to chronic hepatitis, and has been implicated in hepatocellular carcinoma. Hepatitis A and C Viruses also infect the liver cells. Liver cancers such as hepatoblastoma, biliary cancer and liver tumors are intractable and generally lethal diseases. There are also a number of liver-specific diseases, metabolic diseases, and blood disorders that may be treated by gene therapy.

Hemophilia B, or factor IX deficiency, is an X-linked recessive disorder occurring in about 1/25,000 males. Severely affected individuals are at risk for spontaneous bleeding into numerous organs. Bleeding can be life threatening and/or lead to chronic disabilities. The severity of the bleeding tendency is variable between patients and is related to the concentration of functional plasma factor IX. Individuals with >5 to 30% of the normal factor IX have mild hemophilia that may not be recognized until adulthood or following heavy trauma or surgery, see, for example, Reiner & Davie, "Introduction to hemostasis and the vitamin K-dependent coagulation factors" in *The Metabolic Basis of Inherited Disease* (Scriver, Beaudet, Sly & Valle, eds.) Vol. 3, pages 3181–3221 (McGraw Hill, New York, 1995).

Therapy for acute bleeding consists of the transfusion of clotting factor concentrates prepared from human blood and more recently recombinant clotting factors that are currently in clinical trials. Both recombinant retroviral (Kay et al., Science, 262:117–119 (1993)) and adenoviral (Kay et al., Proc. Natl. Acad. Sci. USA, 91:2353–2357 (1994)) vectors transferred a factor IX cDNA into the livers of dogs with hemophilia B.

Recombinant retroviral-mediated gene transfer results in persistent yet subtherapeutic concentrations of factor IX and requires the stimulation of hepatocyte replication prior to vector administration.

Recombinant adenoviral vectors temporarily can cure the coagulation defect in the canine hemophilia B model, however, an immune response directed against viral gene products made by the vector results in toxicity and limited gene expression (Kay et al. (1994); Yang et al., Proc. Natl. Acad. Sci. USA, 91:4407–4411 (1994)).

Thus, there is a tremendous need for safe and effective vectors for transducing normal liver cells or malignant liver cells in vivo or ex vivo. The instant invention provides novel methods and vectors for transducing liver cells to treat diseases and disorders including but not limited to hepatitis, hemophilia, liver disorders, in addition to delivery of therapeutic proteins to the bloodstream.

SUMMARY OF THE INVENTION

The instant invention demonstrates for the first time that recombinant AAV vectors may be used to deliver exogenous or endogenous polynucleotides to the cells of the liver of an intact mammal for effective expression of a gene of interest. The methods and recombinant AAV vectors described herein provide a significant development in the field of recombinant AAV vector gene therapy.

The exogenous or endogenous polynucleotide preferably comprises a gene of interest encoding any diffusible polypeptide, ribozyme, nucleic acid or antisense oligonucleotide for gene therapy. The methods of the invention provide significant advantages, including the ability to deliver rAAV vectors harboring the genes for any diffusible polypeptide or nucleic acid to hepatic tissue via delivery routes such as, but not limited to, intraportal or intravenous administration into an intact animal. The purpose of delivering rAAV vectors to the liver is to obtain therapeutic levels of gene expression in regions proximate to or distant from the liver.

The rAAV vectors of the invention can be used as viral particles alone to transduce cells of the liver. Alternatively, the rAAV vector virus particles can be used in conjunction with additional treatments, including partial hepatectomy or treatment with secondary agents that enhance transduction, whether associated in vivo or ex vivo therapies. Examples of secondary agents include gamma irradiation, UV irradiation, tritiated nucleotides such as thymidine, cis-platinum, etoposide, hydroxyurea, aphidicolin and adenovirus.

Another advantage of the invention is that it permits expression of diffusible polypeptides in the liver which provides access to the circulation and permits systemic delivery of therapeutic proteins and polypeptides of interest that are encoded by an exogenous or endogenous polynucleotide of a rAAV vector.

The invention also provides novel methods of transducing normal liver cells with rAAV vectors either in culture, in vivo or ex vivo and transducing diseased or cancer liver cells in vivo or ex vivo.

DESCRIPTION OF SPECIFIC EMBODIMENTS

Figure 1:
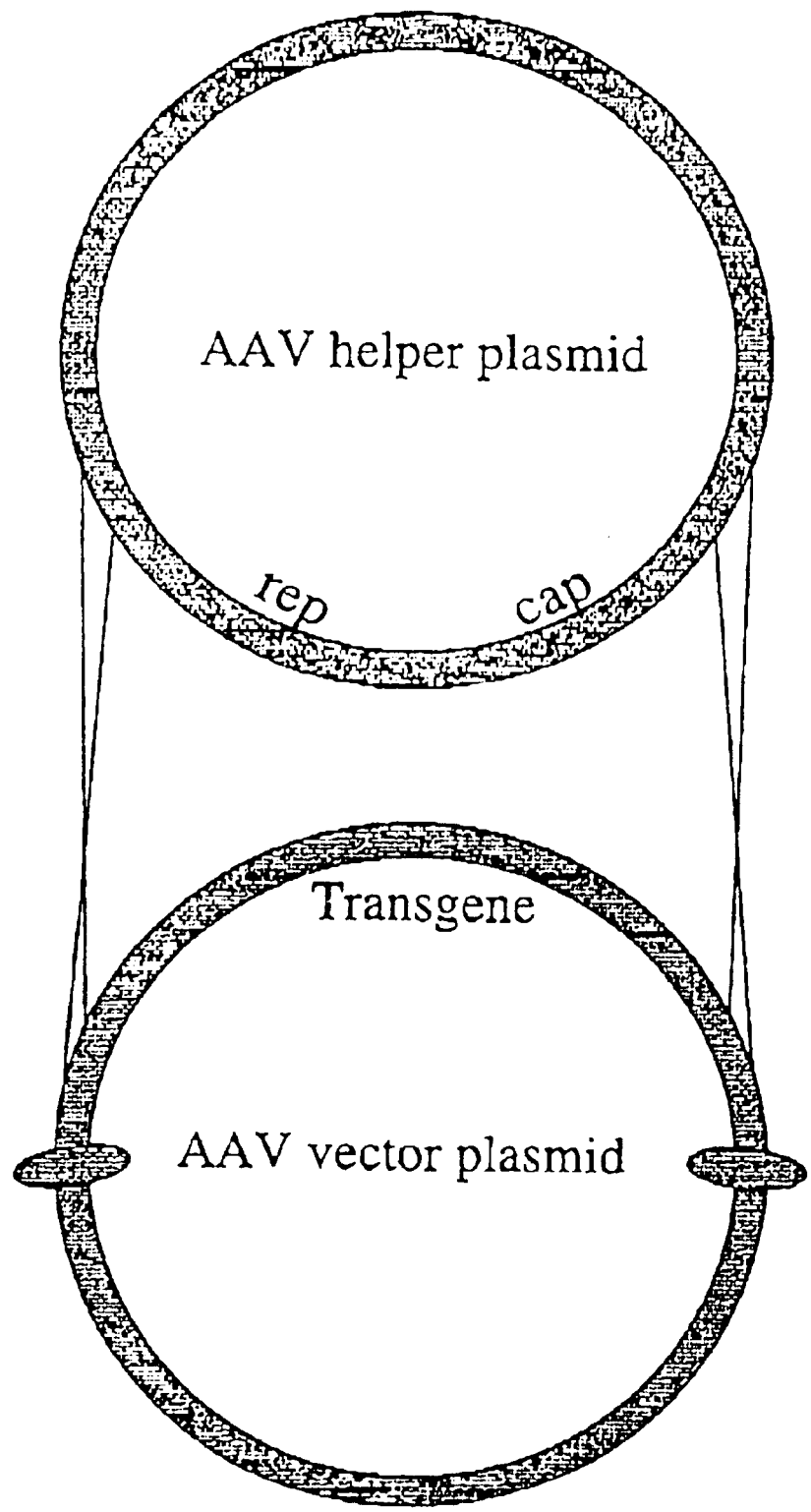
FIG. 1 depicts how recombination can occur between an AAV helper plasmid and an AAV vector plasmid to regenerate a wild-type AAV.

LOCAL AND SYSTEMIC DELIVERY OF THERAPEUTIC AMOUNTS OF RECOMBINANT PROTEINS FROM THE LIVER

The instant invention demonstrates that therapeutic levels of a protein or polypeptide can be achieved locally and systemically by delivering to the liver of a mammal a recombinant AAV vector carrying an exogenous or endogenous polynucleotide encoding that protein or polypeptide. Not only is the protein expressed in the liver but also can be found in the circulation (i.e. blood). No toxicity is observed following delivery of the recombinant protein to the circulation of the animal. There is no observable liver pathology associated with transducing the cells of the liver with an rAAV vector. Lastly, expression of the protein or polypeptide encoded by the exogenous or endogenous polynucleotide in the rAAV vector from the liver can be detected at sites distal to the site of administration. The invention is illustrated by the expression of human Factor IX in immunocompetent and immunocompromised mice via delivery of a rAAV vector comprising an exogenous polynucleotide comprising the human Factor IX polynucleotide.

A number of scientific publications describe the state of the art in the recombinant AAV vector field. The following publications hereby are incorporated by reference:

Afione, Conrad, Kearns, Chunduru, Adams, Reynolds, Guggino, Cutting, Carter and Flotte 1996. In vivo Model of Adeno-Associated Virus Vector Persistence and Rescue. J. Virol., 70:3235–3241.

Flotte, Afione, Conrad, McGrath, Solow, Oka, Zeitlin, Guggino and Carter 1993. Stable in vivo Expression of the Cystic Fibrosis Transmembrane Conductance Regulator with an Adeno-Associated Virus Vector. Proc. Natl. Acad. Sci. USA, 90:10613–10617.

Flotte, Carter, Conrad, Guggino, Reynolds, Rosenstein, Taylor, Walden and Wetzel 1996. A Phase I Study of an Adeno-Associated Virus-CFTR Gene Vector in Adult CF Patients with Mild Lung Disease. Hum. Gene Ther., 7:1145–1159.

Kaplitt, Leone, Samulski, Xiao, Pfaff, O'Mally and During 1994. Long-Term Gene Expression and Phenotypic Correction using Adeno-Associated Virus Vectors in the Mammalian Brain. Nat. Genet., 8:148–154.

Kaplitt, Xiao, Samulski, Li. Kaplitt, Ojamm, Klein, Strumpf, Makimura, Breslow and Diethrich 1996. Long Term Gene Transfer into Porcine Myocardium Following Selective Percutaneous Coronary After Infusion of an Adeno-Associated Virus Vector. Ann. Thorac. Surg., 62:1669–1676.

Lalwani, Walsh, Reilly, Muzyczka and Mhatre 1996. Development of in vivo Gene Therapy for Hearing Disorders: Introduction of Adeno-Associated Virus into the Chochlea of the Guinea Pig. Gene Ther., 3:588–592.

McCown, Xiao, Li, Breese and Samulski 1996. Differential and Persistent Expression Patterns of CNS Gene Transfer by an Adeno-Associated Virus (AAV) Vector. Brain Res., 713:99–107.

Muro-Cacho, Samulski and Kaplan 1992. Gene Transfer in Human Lymphocytes Using a Vector Based on Adeno-Associated Virus. J. Immunother., 11:231–237.

Samulski 1994. Adeno-associated virus vectors. In: Human viruses in gene therapy. pp 53–76

Samulski, Chang and Shenk 1989. Helper-free stocks of recombinant adeno-associated viruses: normal integration does not require viral gene expression. J. Virol., 63:3822–3828.

Snyder, Xiao and Samulski 1996. Production of Recombinant Adeno-Associated Viral Vectors. In Current Protocols in Human Genetics. 12.1.1–24. Dracopoli, Haines, Krof, Moir, Morton, Seidman, Seidman and Smith, eds. John Wiley and Sons Publisher, New York.

Su, Chang, Xu and Kan 1996. Selective Killing of AFP-Positive Hepatocellular Carcinoma Cells by Adeno-Associated Virus Transfer of the Herpes Simplex Virus Thymidine Kinase Gene. Hum. Gene Ther., 7:463–470.

Walsh, Liu, Xiao, Young, Nienhuis and Samulski 1992. Regulated high level expression of a human g-globin gene introduced into erythroid cells by an adeno-associated virus vector. Proc. Natl. Acad. Sci. USA, 89:7257–7261.

Xiao, Li and Samulski 1996. Efficient Long-Term Gene Transfer into Muscle of Immunocompetent Mice by an Adeno-Associated Virus Vector. J. Virol., 70:8098–8108.

THE RAAV VECTORS

The rAAV vectors of the instant invention are derivatives of the adeno-associated virus, into which an exogenous or endogenous polynucleotide has been introduced and of which various sequences may have been modified.

While the wild-type adeno-associated virus is defective in requiring helper virus for lytic infection, there is the possibility that the subject to whom the vector is delivered will harbor a herpesvirus or adenovirus infection which can complement the rAAV vector and lead to a production of rAAV vectors. To guard against that possibility, the rAAV vector is modified to reduce the possibility of rescue. In theory, such modifications can take the form of point mutations of one or more viral genes, which mutations either prevent expression of the gene altogether, or result in the expression of a modified gene product which is nonfunctional. However, point mutations can be reversible. Consequently, it is preferable that each undesired adeno-associated virus gene simply be deleted, which has the additional advantage of creating more room within the viral package for larger foreign nucleic acids.

It is preferable that all of the viral genes be deleted from the rAAV vector, or otherwise inactivated, as in the known AAV vector dl3-94, see, e.g., McLaughlin, J. Virol., 62:1963–1973 (1988). However, it should be understood that a rAAV vector retaining one or more AAV genes, such as the known AAV vector dl52–91, still may be useful for gene delivery, although possibly inferior to a preferred vector containing no functional AAV genes; see Hermonat, J. Virol., 51:329–339 (1984). Preferably, the rAAV vector retains from AAV essentially only the recognition signals for replication and packaging (ITR).

For propagation of the rAAV vector in vitro, susceptible cells are co-transfected with an AAV-derived vector DNA and a suitable AAV-derived helper virus or plasmid harboring the AAV rep gene, AAV cap gene or both and infected by a helper virus, including HSV-1, adenovirus or CMV. The particular method of producing viral particles is not critical to the invention. Any method of producing the rAAV viral particles can be used, including but not limited to that described in Samulski et al. (1989), so long as it results in an appropriate concentration of viral particles capable of transducing cells in vivo and ex vivo. One of ordinary skill in the art will appreciate that any purification method used should produce infectious viral particles able to transduce hepatic cells in vivo or ex vivo.

It is not necessary that the AAV-derived sequences correspond exactly with wild-type AAV prototypes. For example, the rAAV vectors of the instant invention may feature modified inverted terminal repeats and other sequences, provided that the rAAV vector can replicate and be packaged with the assistance of helper virus, and establish a nonpathogenic latent infection in target cells. Another example of an rAAV vector of use in the methods of the invention is the recombinant viral vector system of U.S. Pat. No. 5,478,745.

The rAAV vector may further comprise one or more restriction sites into which an exogenous or endogenous polynucleotide may be cloned without interfering with packaging and replication. Preferably, at least one unique restriction site is provided. The rAAV vector also may comprise one or more marker genes to facilitate genetic manipulation. Suitable marker genes are known in the art and include, but are not limited to, the neomycin and hygromycin resistance genes, bacterial lacZ and the firefly luciferase gene.

THE AAV-DERIVED HELPER VIRUS OR PLASMID

The AAV-derived helper virus or helper plasmid may be any virus or plasmid which is capable, on expression of the AAV genes it carries, of providing proteins necessary for the replication and packaging of the rAAV vector in a suitable host cell, for the purpose of producing rAAV vector stock.

For example, the helper virus may be one in which a gene necessary for replication is made defective. For example, an adenovirus stock wherein a gene thereof, such as the E1A gene, is disabled.

Moreover, in a preferred embodiment, the helper virus or helper plasmid is one which has been engineered to reduce the risk of recombination between the helper DNA and the rAAV vector DNA. Most desirably, there is very limited or no sequence homology between the AAV sequences of the vector DNA and the AAV sequences of the helper DNA. For example, the helper DNA may be an AAV sequence in which the AAV inverted terminal repeats are replaced by the corresponding sequences of another virus, such as adenovirus (e.g., adenovirus type 5 DNA), see Samulski et al., J. Virol., 63:3822–28 (1989).

Helper virus may be removed by heat inactivation at about 56° C. for about 30–45 minutes, or physically separated from packaged rAAV vectors by any of a variety of methods, including single or multiple centrifugation runs in a cesium chloride gradient.

EXOGENOUS AND ENDOGENOUS POLYNUCLEOTIDES

Basic procedures for constructing recombinant DNA and RNA molecules in accordance with the instant invention are disclosed in numerous publications, including Sambrook et al., In: Molecular Cloning: A Laboratory Manual, Second Edition, Cold Spring Harbor Press, Cold Spring Harbor, N.Y. (1989), which is herein incorporated by reference.

The instant invention may be used for gene therapy of genetically-based or genetically-affected disorders. An individual may be in need of gene therapy because, as a result of one or more mutations in the regulatory region and/or the coding sequence of one or more genes, a particular gene product is expressed inappropriately, e.g., has an incorrect amino acid sequence, or is expressed in the wrong tissues or at the wrong times, is underexpressed or overexpressed.

Therefore, the polynucleotide delivered to that individual may be considered exogenous even though it is identical to a gene native to the species of the recipient, provided it differs in at least a single nucleotide in the regulatory or coding region from the cognate gene of the individual to whom it is delivered, and therefore may encode a different or identical gene product or is expressed to a different degree and/or in different cells, under at least some conditions. An endogenous polynucleotide of the invention is identical to one which is normally expressed in the individual to whom the rAAV vector is administered, but prior to administration, is expressed at inappropriate levels or not expressed in certain types of cells.

The exogenous polynucleotides of the instant invention can be exogenous to both AAV and to the target cell.

The polynucleotides of the invention may be any nucleic acids, including DNA or RNA, synthetic DNA, modified DNA, complementary DNA, genomic DNA or any combinations or hybrids thereof. The polynucleotides may be of any sequence or length, provided that they may be incorporated into the rAAV vector, delivered to target cells and expressed in target cells. Typically, because of the packaging limitations of AAV, the polynucleotides can have a length of up to about 10,000 bases. Preferably, the polynucleotides are 100 to 5,000 bases in length.

As noted herein, the polynucleotide of interest also is identified as a transgene.

POTENTIAL DISEASE TARGETS

Because the instant invention is directed to methods of expressing exogenous or endogenous polynucleotides in cells of the liver and delivery of the expressed polypeptides to sites proximal to and distal from the liver, including the circulating blood, there are a number of potential diseases for which the invention can be useful, including but not limited to the following disorders and relevant genes. One of ordinary skill in the art will appreciate that the instant invention can be used with any number of polynucleotides. The following are examples of polynucleotides, and one of ordinary skill in the art can select any desirable polynucleotide for gene therapy from any number of sources, including Internet searches, for example, the Genbank database can be found at the following web address: http://www3.ncbi.nlm.nih.gov. Also, reference can be made to any of a number of medical genetics resources.

BLOOD DISEASES

Hemophilia B (factor IX, Genbank Accession J00136, J00137), Hemophilia A (factor VIII, Genbank Accession M14113), albuminemia (albumin, Genbank Accession W77778, A06977), SCID (adenosine deaminase, Genbank Accession U73197).

METABOLIC DISEASES

Familial hypercholesterolemia (LDL receptor, Genbank Accession P01130, D16493), Gaucher's disease (β-glucocerebrosidase, Genbank Accession M16328, M11080), Sly's Syndrome (glucuronidase, Genbank Accession M15182), Chronic obstructive pulmonary disease (α1-antitrypsin, Genbank Accession K01396), PKU (phenylalanine hydroxylase, Genbank Accession K03020) and urea cycle disease (ornithine transcarbamylase, Genbank Accession K02100).

LIVER-SPECIFIC DISEASES

Crigler-Najjar type 1 (UDP-glucuronosyltransferase, Genbank Accession Y00317), tyrosinemia type 1 (fumaryl acetoacetate hydrolase, Genbank Accession S63548, S63549) and glycogen storage diseases (Glucose-6-Phosphatase, Genbank Accession U01120, X96937).

LIVER TUMORS

Liver tumors are intractable and usually lethal diseases which largely derive from infection by hepatitis viruses or by metastasis of other cancers (e.g. colon, breast, melanoma). Primary liver cancer disease (e.g. hepatoblastoma, biliary cancer) also arises by unknown mechanisms. Currently, treatment modalities have been largely ineffectual. A recent strategy using gene therapy as a possible approach to tumor therapy involves the insertion of the thymidine kinase (TK) gene from herpes simplex virus type 1 into a replication-deficient retroviral vector or adenoviral vector. However, in contrast to the instant invention, the retroviral vector only transferred the TK gene into dividing tumor cells, but not into either non-dividing tumor cells or healthy liver tissue.

Cells transduced with TK via the retroviral vector became susceptible to cytotoxicity by the drug ganciclovir. TK phosphorylates ganciclovir, which in phosphorylated form disrupts DNA replication and kills dividing cells. Even nearby dividing cells not transduced with TK can be killed. The phenomenon is referred to as the "bystander effect."

One embodiment of the current invention envisions a significant improvement over these previous studies, namely, insertion of the TK gene (EMBL HEHSV1TK, Accession X03764; EMBL HEHS07, Accession V00466), into an AAV vector, which should permit transduction of genes into dividing tumor cells with efficiencies that are at least equal to retroviral vectors, and possibly with greater efficiency. Unlike retroviruses, however, AAV vectors also will transfer the TK gene into slowly dividing or non-dividing cells within tumors as well as non-dividing normal cells. This provides two significant advantages of the instant invention as compared with retroviral vectors.

First, the ability to phosphorylate drugs within non-dividing tumor cells and normal cells should create a greater pool of activated drug within the tumor. Given the observation of the bystander effect, non-dividing tumor cells containing the rAAV vector comprising the HSV TK gene can phosphorylate the drug which then could enter a nearby dividing cell which may not have been transduced with the viral gene. Thus, a non-dividing cell could permit destruction of a nearby, non-transduced cell, even though the transduced, non-dividing cell would not be effected adversely. In that manner, a greater population of dividing cells would be destroyed.

The second advantage also involves the ability of rAAV vectors to transduce non-dividing cells. If a retrovirus enters a non-dividing cell, reverse transcription does not occur and the vector is lost. Since retroviral vectors are lost in non-dividing cells and other DNA viral vectors are not maintained reliably within the host genome, the ability to retain the TK gene if a quiescent cell begins division is a property unique to an rAAV vector. Finally, it should be reiterated that stable maintenance of the rAAV vector should not result in disruption or abnormal regulation of host genes and that transduction of normal non-dividing cells with TK should not have any adverse effects, since it is the subsequent activation of the drug by TK which blocks DNA replication and that only results in destruction of dividing cells. Thus, this embodiment of the invention provides substantial improvements over previous drug-susceptibility tumor treatment strategies.

Other exogenous or endogenous polynucleotides that can be used in the rAAV vectors described herein include any polynucleotide that encodes a diffusible polypeptide, i.e. a polypeptide that can diffuse from the site of administration to effect systemic delivery or a diffusible polynucleotide or ribozyme. For example, diffusible polypeptides that may be useful for gene therapy include insulin, Factor VIII, cytokines, including interferons (IFN-α, IFN-β, IFN-γ), interleukins, GM-CSF (granulocyte-macrophage colony-stimulating factor), M-CSF (macrophage colony-stimulating factor), tumor necrosis factors, growth factors (TGF-β (transforming growth factor-β) and PDGF (platelet-derived growth factor)). It will be apparent to one of ordinary skill in the art that the methods described herein can be used to express any diffusible polypeptides of therapeutic interest. The exogenous or endogenous polynucleotide also may be an antisense polynucleotide or ribozyme.

TARGET CELLS

The target cells of the vectors of the instant invention are cells of the hepatic system of a mammal. In one embodiment, the cells are normal cells cultured in vitro.

In another embodiment, the cells are part of a living mammal at the time the rAAV vector is delivered to the cell. The mammal may be at any stage of development at the time of delivery, e.g., embryonic, fetal, infantile, juvenile or adult. Additionally, the cells may be healthy or diseased.

To deliver the vector specifically to a particular region of the liver, it may be administered by intraportal injection, as exemplified in Examples 6–9. Because the AAV vector will be maintained stably in the target cells, rather than producing viral particles, the subsequent spread of the vector will be minor and will be mainly a function of passive diffusion from the site of injection. The degree of diffusion may be controlled by adjusting the ratio of rAAV vector to fluid carrier.

In certain embodiments, the vector will be administered via an intravascular approach. For example, the vector will be administered intra-arterially. Of course, with intravenous as well as intraportal delivery, the recipient mammal must be able to tolerate the possibility of delivery of the vector to cells other than those of the hepatic system.

For targeting the vector to a particular type of cell, e.g., hepatocytes, it may be necessary to associate the vector with a homing agent that binds specifically to a surface receptor of the cell. Thus, the vector may be conjugated to a ligand (e.g., galactose) for which certain hepatic system cells have receptors. The conjugation may be covalent, e.g., a crosslinking agent such as cross-linking agents (e.g. glutaraldehyde), or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

Whatever the form of conjugation, it must not interfere substantially either with the production or transduction of the rAAV vector.

The target cells may be human cells, or cells of other mammals, especially nonhuman primates and mammals of the orders Rodenta (mice, rats, rabbit, hamsters), Carnivora (cats, dogs), and Arteriodactyla (cows, pigs, sheep, goats, horses).

TRANSDUCTION EFFICIENCY

The rAAV vectors may be administered as viral particles alone, whether as an in vivo direct delivery to the portal vasculature or as an ex vivo treatment comprising administering the rAAV vector viral particles in vitro to cells from the animal receiving treatment followed by introduction of the transduced cells back into the donor. Alternatively, the rAAV vector virus particles can be used to transduce cells in conjunction with secondary agents known to enhance the efficiency of transduction, see, e.g., PCT/US95/07202, for a variety of secondary agents. Secondary agents useful for enhancing transduction efficiency include radioactive molecules, including tritiated nucleotides, ultraviolet radiation, gamma irradiation, cis-platinum, hydroxyurea, etoposide, camptothecin, aphidicolin and adenovirus, see e.g., Ferrari et al., J. Virol., 70:3227–3234 (1996).

GENE EXPRESSION

When the exogenous or endogenous polynucleotide comprises an expressible gene, the gene may be one which: occurs in nature, is a non-naturally occurring gene which nonetheless encodes a naturally occurring polypeptide or is a gene which encodes a recognizable mutant of such a polypeptide. The exogenous or endogenous polynucleotide also may encode an mRNA which will be "antisense" to a DNA found, or an mRNA normally transcribed, in the host cell, but which antisense RNA is not itself translatable into a functional protein. Additionally, the exogenous or endogenous polynucleotide may encode a ribozyme or any other protein or polypeptide or fragment thereof having a regulatory or therapeutic effect.

The precise nature of regulatory regions needed for gene expression may vary from organism to organism, but in general include a promoter which directs the initiation of RNA transcription. Such regions may include those 5'-non-coding sequences involved with initiation of transcription such as the TATA box. The promoter may be constitutive or regulatable. Constitutive promoters are those which cause an operably linked gene to be expressed essentially at all times. Regulatable promoters are those which can be activated or deactivated. Regulatable promoters include inducible promoters, which are usually "off" but which may be induced to turn "on", and "repressible" promoters, which are usually "on" but may be turned "off". Many different regulators are known, including temperature, hormones, cytokines, heavy metals and regulatory proteins. The distinctions are not absolute; a constitutive promoter may be regulatable to some degree.

The regulatability of a promoter may be associated with a particular genetic element, often called an "operator", to which an inducer or repressor binds. The operator may be modified to alter its regulation. Hybrid promoters may be constructed in which the operator of one promoter is transferred into another.

The promoter may be a "ubiquitous" promoter active in essentially all cells of the host organism (e.g. the beta-actin or cytomegalovirus promoters), or it may be a promoter whose expression is more or less specific to the target cells (albumin promoter). Preferably, the tissue-specific promoters are essentially not active outside the hepatic system and the activity of the promoter optionally may be higher in some components of the hepatic system than in others.

Thus, the promoter may be one which is active primarily in the hepatic system. The specificity may be absolute or relative. Similarly, the promoter may be specific for particular cell types, including but not limited to hepatocytes, Kupffer cells, or endothelial cells.

In general, to find a tissue-specific promoter, one identifies a gene which is expressed only (or primarily) in that tissue and then isolates the gene encoding that protein. (The gene may be a normal cellular gene, or a viral gene of a virus which infects that cell). The promoter of that gene is likely to retain the desired tissue-specific activity when linked to another gene. The tissue specificity of a promoter may be associated with a particular genetic element, which may be modified or transferred into a second promoter.

One of ordinary skill in the art will appreciate that a tissue-specific promoter for use in an AAV vector may be selected from any of the known liver-specific promoters and enhancers, including the albumin promoter, the alphafetoprotein promoter (Genbank Accession No. L34019), alphafetoprotein enhancer, human apolipoprotein E (ApoE) gene promoter and its associated liver-specific enhancers HCR-1 and HCR-2 (Nguyen et al., Oncogene, 12(10):2109–2119 (1996) and Allen et al., J. Biol. Chem., 270(44): 26278–26281 (1995)), the liver-specific enhancer of apolipoprotein AI (Malik et al., Mol. Cell. Biol., 16(4):1824–1831 (1996)) and the liver-specific human α1-antitrypsin promoter (Wu et al., Hum. Gene Therapy, 7(2):159–171 (1996) and Hafenrichter et al., Blood, 84(10):3394–3404 (1994)).

There also are other known strong promoters which find common use to obtain high levels of recombinant protein expression. For example, the herpes simplex thymidine kinase promoter, SV40 promoter and LTR's have found wide use as strong promoters. An example is the LTR obtained from Moloney leukemia retrovirus.

For the gene to be expressible, the coding sequence must be operably linked to a promoter sequence functional in the target cell. A promoter region would be operably linked to a coding sequence if the promoter were positioned so that, when the promoter was activated, the coding sequence was transcribed. The coding sequences are operably linked if the linkage does not cause an error in the reading of the downstream sequence. In order to be "operably linked" it is not necessary that two sequences be immediately adjacent to one another.

If desired, the non-coding region 3' to the gene sequence coding for the desired RNA product may be obtained. The region may be retained for its transcriptional termination regulatory sequences, such as those which provide for termination and polyadenylation. Thus, by retaining the 3'-region naturally contiguous to the coding sequence, the transcriptional termination signals may be provided. Where the transcriptional termination signals natively associated with the coding sequence are not satisfactorily functional in the expression host cell, then a different 3' region, functional in the host cell, may be substituted.

In addition to or instead of an expressible gene as the exogenous or endogenous polynucleotide, the exogenous or endogenous polynucleotide may comprise sequences homologous to genetic material of the target cell, whereby it may insert into the genome by homologous recombination, thereby displacing a coding or control sequence of a gene or deleting a gene altogether, provided that the sequences do not interfere substantially with stable maintenance of AAV vector sequences. rAAV vectors that are maintained stably in a target cell may be integrated into the host cell genome, may be maintained episomally or may be maintained as a combination of integrated rAAV vectors and episomally maintained rAAV vectors.

In another embodiment, the exogenous or endogenous polynucleotide is "antisense" to a genomic or other DNA sequence of the target organism (including viruses and other pathogens) or to a messenger RNA transcribed in cells of the organisms, which hybridizes sufficiently thereto to inhibit the transcription of the target genomic DNA or the translation of the target messenger RNA. The efficiency of such hybridization is a function of the length and structure of the hybridizing sequences. The longer the sequence and the closer the complementarily to perfection, the stronger the interaction. As the number of base pair mismatches increases, the hybridization efficiency will fall off. Furthermore, the GC content of the packaging sequence DNA or the antisense RNA will also affect the hybridization efficiency due to the additional hydrogen bond present in a GC base pair compared to an AT (or AU) base pair. Thus, a target sequence richer in GC content is preferable as a target.

It is desirable to avoid antisense sequences which would form secondary structure due to intramolecular hybridization, since that would render the antisense nucleic acid less active or inactive for its intended purpose. One of ordinary skill in the art will readily appreciate whether a sequence has a tendency to form a secondary structure. Secondary structures may be avoided by selecting a different exogenous or endogenous polynucleotide.

In yet another embodiment, the exogenous or endogenous polynucleotide encodes a ribozyme, i.e., an RNA with a desirable enzymatic activity to treat hepatitis or any other liver or blood disorder.

RECOMBINANT VIRUS PREPARATION

Figure 2:
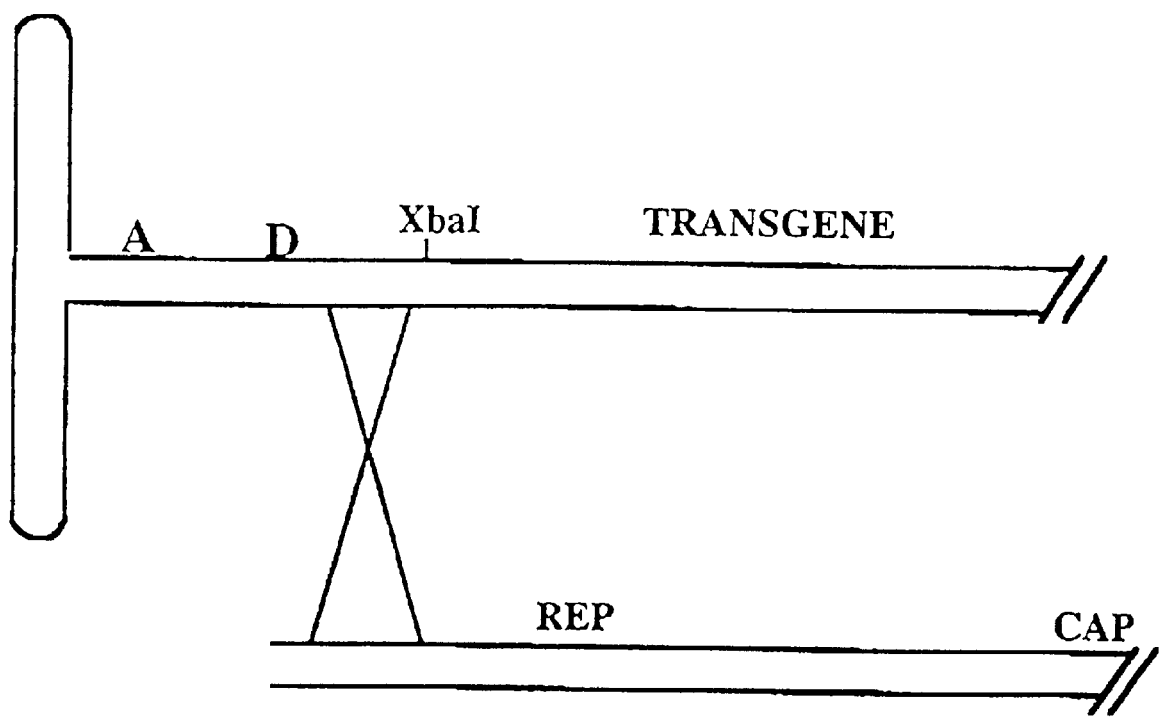
FIG. 2 depicts where such a cross over event could occur.

Prior to administration to a host, it is beneficial to determine the purity of the recombinant AAV preparation, that is, the AAV vector containing the transgene. For example, while no diseases are associated with AAV infection, knowing the degree of wild-type AAV contamination in a recombinant virus preparation is desirable. Wild-type virus can be generated by cross over between, for example, the AAV helper plasmid and the AAV plasmid carrying the transgene, see FIGS. 1 and 2.

The presence of contaminating wild-type AAV can be determined, for example, by a nucleic acid amplification assay, such as PCR or an RNA based amplification method such as 3SR (Gingeras et al., Ann. Biol. Clin., 48:498–501 (1990)) and NASBA (van der Vliet et al., J. Gen. Micro., 139:2423–2429 (1993)).

Thus, in the case of PCR, AAV nucleic acid is prepared and subjected to a PCR reaction, along with positive and negative controls. The strategic identification of certain PCR primers enables distinguishing wild-type from recombinant virus in an expeditious and efficient fashion which is another embodiment of the instant invention. Thus, primers are selected to be specific for wild-type AAV or for wild-type AAV derived through recombination of the helper and vector plasmids.

Figure 3:
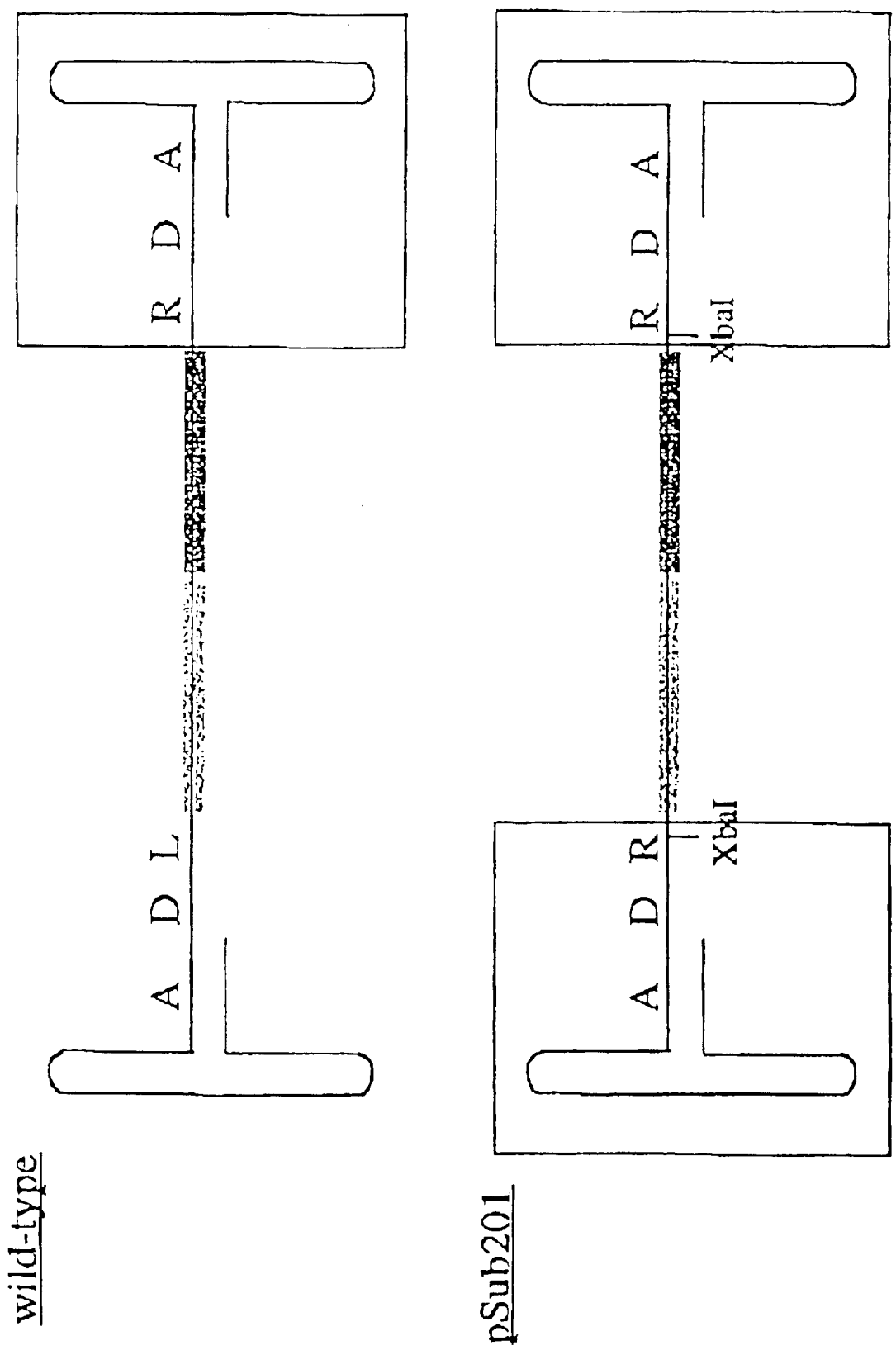
FIG. 3 compares the order of loci on the wild-type AAV and pSub201 cloning vector. A and D are the known A and D regions of AAV; L represents unique sequences found in the region near the left inverted repeat and R represents unique sequences found in the region near the right inverted repeat.

AAV vectors derived from pSub201 (Samulski et al., J. Virol., 61:3096–3101 (1987)), see FIG. 3, or other vectors tailored to have distinctive sequences in the left and right arms of the vector enable distinguishing wild-type virus from wild-type virus arising from recombination. By left and right arms, it is meant to refer to those portions of the vector which flank the cloning site which contains the transgene. Thus, in the case of pSub201, the left arm is that portion to the left of the XbaI site and the right arm is that portion to the right of the XbaI site. The arms contain the hairpin structures.

Referring to the exemplified pSub201 vector to explain the method, it is noted that the pSub201 has sequences found normally on the right arm of AAV are on both sides of the transgene. Thus, sequences found normally only on the right arm are present on the left arm as well, the left sequences having been deleted.

Accordingly, primers can be configured wherein the presence or absence of left sequences or the presence of right sequences on both sides of the virus can be used to distinguish wild-type AAV containing the normally occurring left sequences from any wild-type AAV generated by recombination between the helper and vector plasmids containing right sequences on both sides of the transgene.

For example, when using a pSub201 vector, or equivalent vector containing right arm sequences on both arms, the following primers can be used: D1 (5'ACTCCATCACTAGGGGTTCC3')(SEQ ID NO:1) which is in the AAV ITR; D2 (5'GGTAATGATTAA-CCCGCCATGCTACTTATC3')(SEQ ID NO:2) also in the AAV ITR; AAV2S2 (5'TCAGAATCTGGCGGCAA-CTCCC3')(SEQ ID NO:3) in the AAV rep gene; Splice1 (5'TCGTCAAAAAGGCGTATCAG3')(SEQ ID NO:4) in the AAV splice region; CAP2 (5'TCCCTTGTCGAGTCC-GTTGA3')(SEQ ID NO:5) in the AAV cap gene; and CAP1 (5'CAGAAGGAAAACAGCAAACG3')(SEQ ID NO:6) also in the AAV cap gene.

Figure 4:
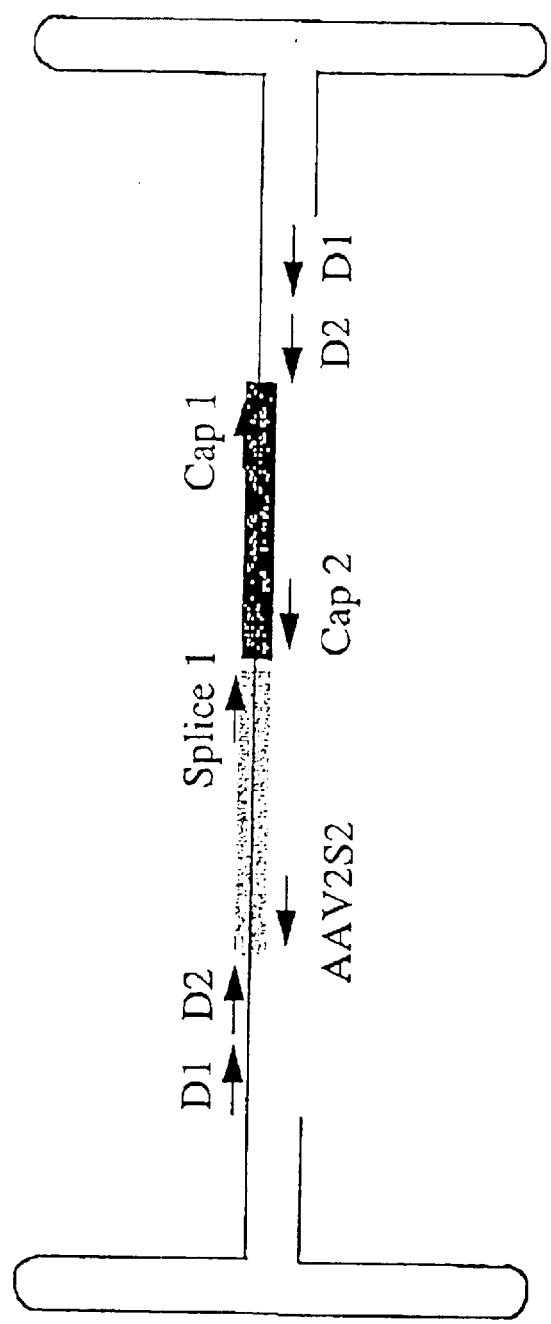
FIG. 4 depicts the location and binding orientation of the exemplified PCR primers.

The site where the primers bind and the direction in which the primer initiates synthesis is summarized in FIG. 4. Thus, primers D1 and AAV2S2 detect left end sequences of wild-type virus and primers D2 and AAV2S2 detect left end sequences in wild-type virus arising from recombination between the vector and helper plasmids. Primers Splice1 and CAP2 detect internal sequences and primers CAP1 and D2 detect right end sequences in both wild-type AAV and wild-type AAV arising from recombination between the vector and helper plasmids.

Figure 5:
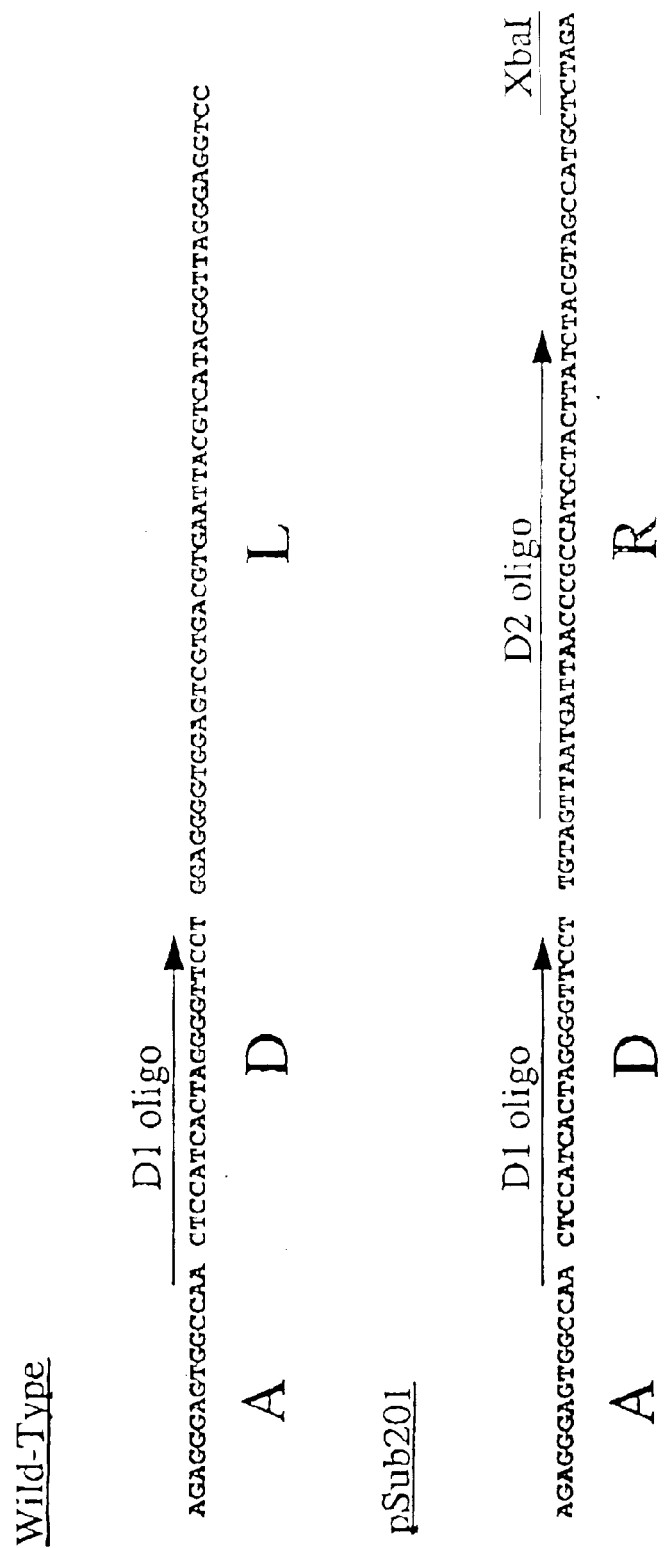
FIG. 5 depicts the location and orientation of binding of the D1 and D2 primers, which can distinguish wild-type AAV from those generated by recombination between the vector and helper plasmids. The wild type sequence is SEQ ID NO:7 and the pSub201 sequence is SEQ ID NO:8.

It can be seen that the combination of D1, D2 and AAV2S2 can be used to distinguish wild-type virus from wild-type virus generated by recombination, see FIG. 5 which depicts when and where the primers bind to target.

It will be appreciated that other sequences specific to the wild-type virus and to cross over generated wild-type virus can be used without departing from the spirit of the instant assay. Thus, the specific primers disclosed herein are for exemplification purposes only and should not be construed to limit the diagnostic assay disclosed herein.

Moreover, as to the primers, it will be well appreciated that once suitable sites are located in the two genomes which are found to be diagnostic of wild-type and cross over generated wild-type virus, the exact nucleotide sequence and length of any one primer can be varied without detracting from the object of the diagnostic assay. The limitations to the variations to the primers depend on, for example, the reaction conditions of PCR to assure hybridization of the primer to target.

In the case of NASBA or 3SR, essentially the same primers can be used, such as D1 and D2 which are diagnostic to wild-type AAV and cross over generated AAV, wherein D1 and D2 are configured to contain at the 3' end thereof a suitable RNA polymerase promoter. Another primer for synthesis of the double-stranded intermediate can rely on, for example, use of the Cap2 or AAV2S2 primers.

METHODS OF ADMINISTRATION OF RAAV VECTORS

The instant invention includes pharmacological intervention in vivo or ex vivo to treat a variety of human disorders, including liver diseases and diseases that can be treated by systemic delivery of a therapeutically effective amount of a polypeptide. The rAAV vector, which comprises the rAAV vector (including the ITR's) packaged in viral particles, are administered to a human patient in an amount effective to obtain the desired concentration of the therapeutic polypeptide encoded by the rAAV vector in the serum, the liver or the target cells. Administration can be by any means in which the therapeutic polypeptides are delivered to the desired target cells. For example, both in vivo and ex vivo methods are contemplated. Intravenous injection of rAAV vector to the portal vein is a preferred method of administration. Other in vivo methods include, for example, direct injection into the lobes of the liver or the biliary duct and intravenous injection distal to the liver. Ex vivo modes of administration include transduction in vitro of resected hepatocytes or other cells of the liver with the rAAV vector, followed by infusion of the transduced, resected hepatocytes back into the portal vasculature or biliary tree of the human patient, see e.g., Grossman et al., Nature Genetics, 6:335–341 (1994).

Whether the transduction of liver cells occurs in vivo or ex vivo, the rAAV vector virus particles can be delivered either alone or in conjunction with a partial hepatectomy, a helper virus (including, for example, adenovirus, CMV or HSV-1) or a secondary agent for enhancing transduction efficiency.

The effective amount of rAAV vector to be administered will vary from patient to patient and according to the therapeutic polypeptide of interest. Accordingly, effective amounts are best determined by the physician administering the rAAV vector and appropriate dosages can be determined readily by one of ordinary skill in the art. A useful initial amount for administration may be in the range from $10^9$ to $10^{20}$ particles for a 70 kg adult. After allowing sufficient time for the rAAV vector to be expressed (typically 4–15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the rAAV viral vectors, see e.g., Vilquin et al., Human Gene Ther., 6:1391–1401 (1995).

Formulations for both ex vivo and in vivo administrations include suspensions in liquid or emulsified liquids. The active ingredient (rAAV vector) often is mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The invention now being generally described, the same will be better understood by reference to the following examples, which are provided for purposes of illustration only and are not to be considered limiting of the invention.

EXAMPLES

Current approaches to the transfer of genes into the hepatic system employ either recombinant viral vectors which retain viral genes, or defective vectors containing residual and potentially dangerous helper viruses. Recombinant adeno-associated viral (rAAV) vectors are non-pathogenic DNA vectors in which all viral genes are removed (96% of the viral genome) which can be maintained stably and from which helper virus essentially is eliminated. In the following examples, an rAAV vector expressing human factor IX is injected intraportally into the mouse liver. Transduced gene expression is detected almost a year post-injection at sites distal from the site of administration. There is no evidence of pathology or toxicity in any animal treated with rAAV vectors.

Example 1

CREATION OF A RECOMBINANT ADENO-ASSOCIATED VIRUS (RAAV) VECTOR FOR GENE TRANSFER INTO LIVER

Figure 11:
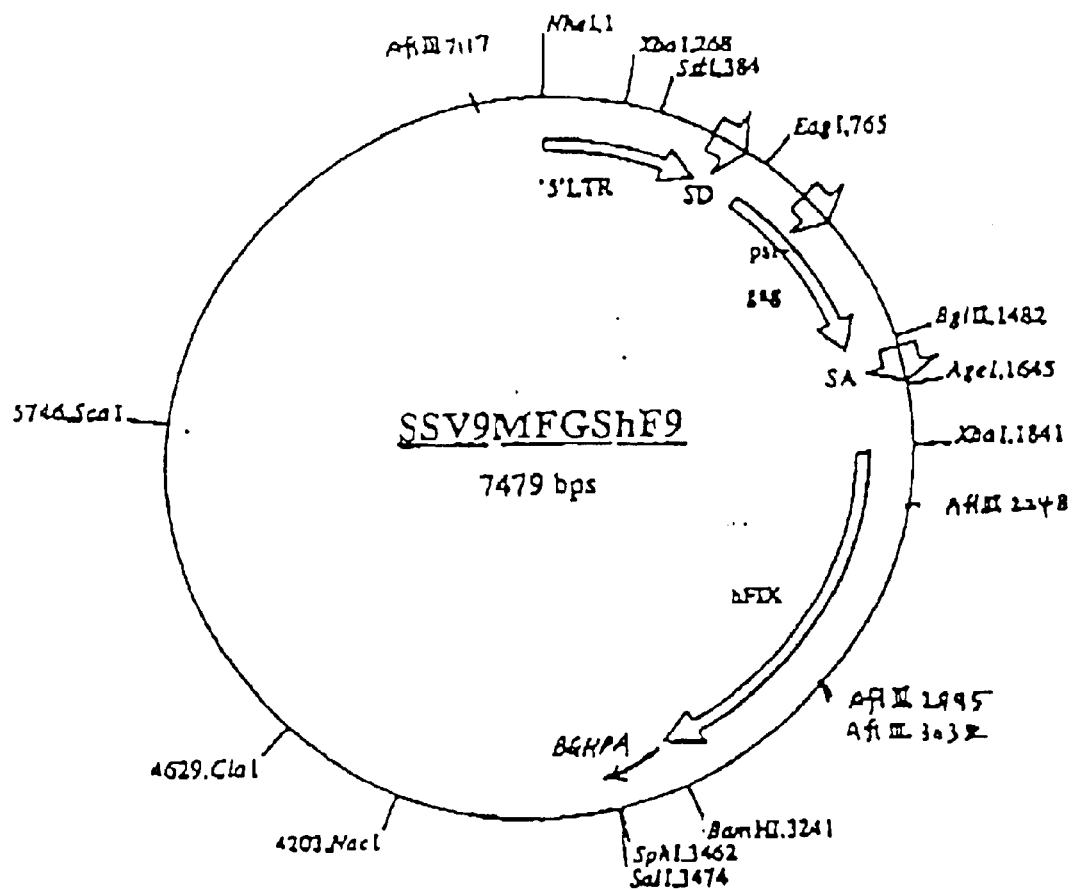
FIG. 11 is a diagram of the SSV9-MFG-S huFIX vector plasmid.

SSV9-MFG-S-huFIX, depicted in FIG. 11, is constructed by digestion of the SSV9-MFG-S-K9F9 vector with AgeI and BamHI to remove the canine Factor IX sequences, followed by ligation with a 1.6 kbp AgeI/BamHI fragment containing the human factor IX sequence from plasmid MFG-S-huFIX (human FIX). The MFG-S-huFIX vector contains the Moloney murine leukemia virus (MLV) 5' LTR (MFG), adjacent MLV splice donor/acceptor (S) and the huFIX cDNA sequence connected to the MLV env ATG and a poly(A) site of bovine growth hormone from pRc/CMV (Invitrogen). The huFIX sequence may be obtained from pAFFIXSVNeo (St. Louis and Verma, Proc. Natl. Acad. Sci. USA, 85:3150–3154 (1988)).

Figure 6:
FIG. 6 is a schematic representation of the rAAV-MFG-human-Factor IX vector. ITR=AAV Inverted Terminal Repeat. MFG Promoter=Murine Moloney Virus Long Terminal Repeat. mULV IVS=mRNA splice donor/splice acceptor. Human FIX=human Factor IX gene. bGH pA=bovine growth hormone polyadenylation site.

The SSV9-MFG-S K9F9 intermediate vector is derived from pXCJL-K9F9 and SSV9. The SSV9 plasmid (Samulski et al., J. Virol., 63:3822–28 (1989)) is digested with XbaI to remove nearly the entire AAV genome leaving only the terminal repeats and filled in with Klenow fragment. The blunt-ended vector is ligated to a 3.24 kilobase pair NheI-SalI fragment (filled in with Klenow fragment) containing the Moloney murine leukemia virus (MLV) 5' LTR, adjacent MLV splice donor/acceptor sequences and K9FIX cDNA sequence connected to the MLV env ATG from plasmid MFG-S-K9FIX and the poly(A) site of bovine growth hormone from pRc/CMV(Invitrogen). For a description of MFG-S, see Dranoff et al., Proc. Natl. Acad. Sci. USA, 90:3539–3543 (1993). The K9FIX cDNA in MFG-S-K9FIX may be obtained from LNCIXL (Dai et al. (1992), Proc. Natl. Acad. Sci. USA, 89:10892–10895) (FIG. 6 and FIG. 11).

Example 2

PACKAGING OF THE RECOMBINANT AAV VECTORS

The recombinant AAV vectors are packaged as described by Snyder et al., in Current Protocols in Human Genetics, pp. 12.1.1–12.1.24, Dracopoli et al., eds. (John Wiley & Sons, New York, 1996).

Figure 7:
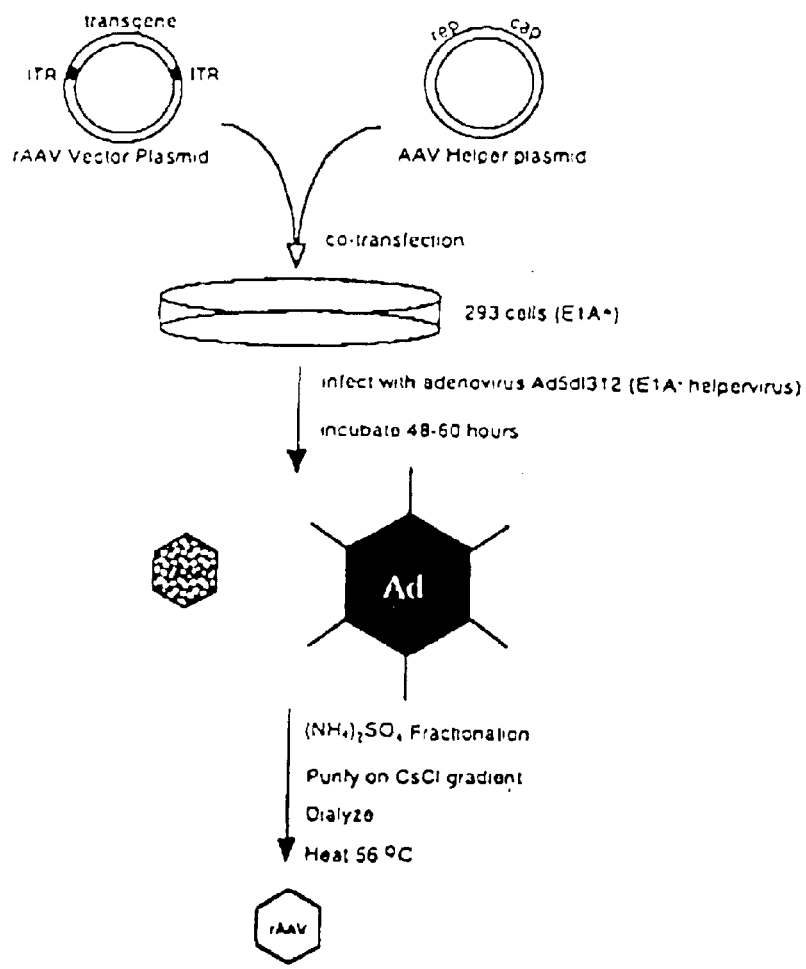
FIG. 7 is a schematic diagram outlining the relationship of the AAV helper plasmid, AAV vector plasmid, adenovirus helper virus and 293 cells for the production of rAAV vectors.

To create rAAV viral vectors, plasmid pSSV9-MFG-S huFIX is co-transfected along with an AAV helper plasmid (which provides necessary AAV replication and structural proteins but lacks AAV termini and thus cannot package into virus) via the calcium phosphate method into 293 cells (Graham et al., J. Gen. Virol., 36:59–74 (1977)), which constitutively express the adenovirus E1a protein. A suitable helper plasmid is pDCG2-1 (Li, Samulski & Xiao, J. Virol., 71:5236–5343 (1997)). The next day, the co-transfected 293 cells are infected with an adenovirus type 5 strain, adenovirus strain dl312 (Jones & Shenk, Cell, 17:683–689 (1979)) to provide remaining replication and packaging machinery. Following full cytopathic effect, virus is harvested by multiple freeze/thaw cycles and purified according to Snyder et al. (1996). A suitable nuclease to remove unwanted nucleic acids is Benzonase (Nycomed, Copenhagen, Denmark) at 250 U/ml. The resulting viral stock consists of packaged rAAV vectors (AAV-human-Factor IX or AAV-hF9) and progeny helper adenovirus. The helper virus essentially is eliminated by purification on cesium chloride (CsCl) density gradients. Viral stocks then are heated to 56° C. for 30 min. to inactivate residual helper adenovirus (Samulski et al. (1989)). Vector titers are obtained by dot-blot hybridization (Snyder et al. (1996)). See FIG. 7 for a depiction of the process.

Example 3

ANIMAL PREPARATION

Either C57BL/6 mice (immunocompetent) or BALB/c SCID mice (immunocompromised) are used for animal studies. Animals are treated according to the NIH Guidelines for Animal Care and Use. For surgical procedures, animals are anesthetized with 0.5 ml of 20 mg/ml Avertin, a midline abdominal incision is made, the abdominal wall is opened, the portal vein is exposed, a cannula is placed into the portal vein and then the abdomen is sutured closed (Vrancken Peeters et al., BioTechniques, 20:278–285 (1996)). Infusions of the AAV vectors are accomplished by connecting the cannula to a syringe pump at a rate of 200 $\mu$l/10 min.

Example 4

HUMAN FACTOR IX ELISA

Mouse blood is collected by retro-orbital bleeding and tested by an ELISA assay using polyclonal antisera to human factor IX, see for example Kay et al. (1994) and Bray et al., J. Lab. Clin. Med., 107:269–278 (1986).

Example 5

FACTOR IX EXPRESSION IN IMMUNOCOMPETENT MICE

Figure 8:
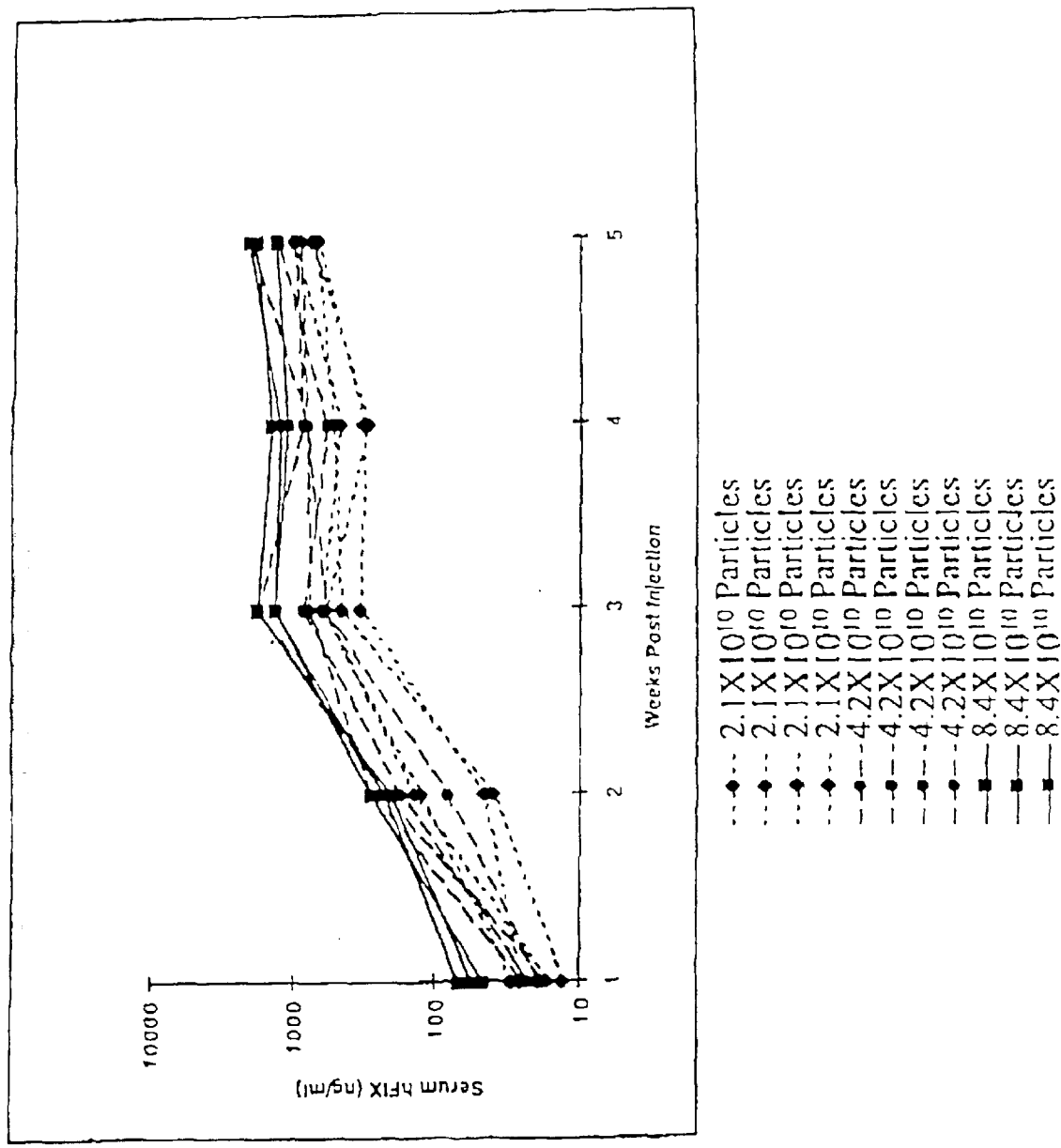
FIG. 8 is a graph showing high-level expression of human Factor IX in immunocompetent mice that were injected intraportally with $2.1 \times 10^{10}$, $4.2 \times 10^{10}$ and $8.4 \times 10^{10}$ particles of rAAV-MFG-hFactor IX.

Recombinant AAV-MFG-Human Factor IX is delivered to the liver as a single intraportal administration of either $2.1 \times 10^{10}$, $4.2 \times 10^{10}$ or $8.4 \times 10^{10}$ particles in a volume of 200 $\mu$l of Dulbecco's Modified Eagle's Medium (DMEM) to C57BL/6 mice (each dose of recombinant AAV vector is administered to groups of three or four mice). Mice are bled at the indicated number of weeks after administration depicted in FIG. 8 and the blood samples are stored frozen. The expression of human Factor IX is determined by ELISA assays using polyclonal antibodies to human Factor IX as described in Example 4.

As a control, the gene for human tyrosine hydroxylase (TH), a protein not expressed in liver, was cloned into the same AAV vector and introduced into animals as described.

Figure 9:
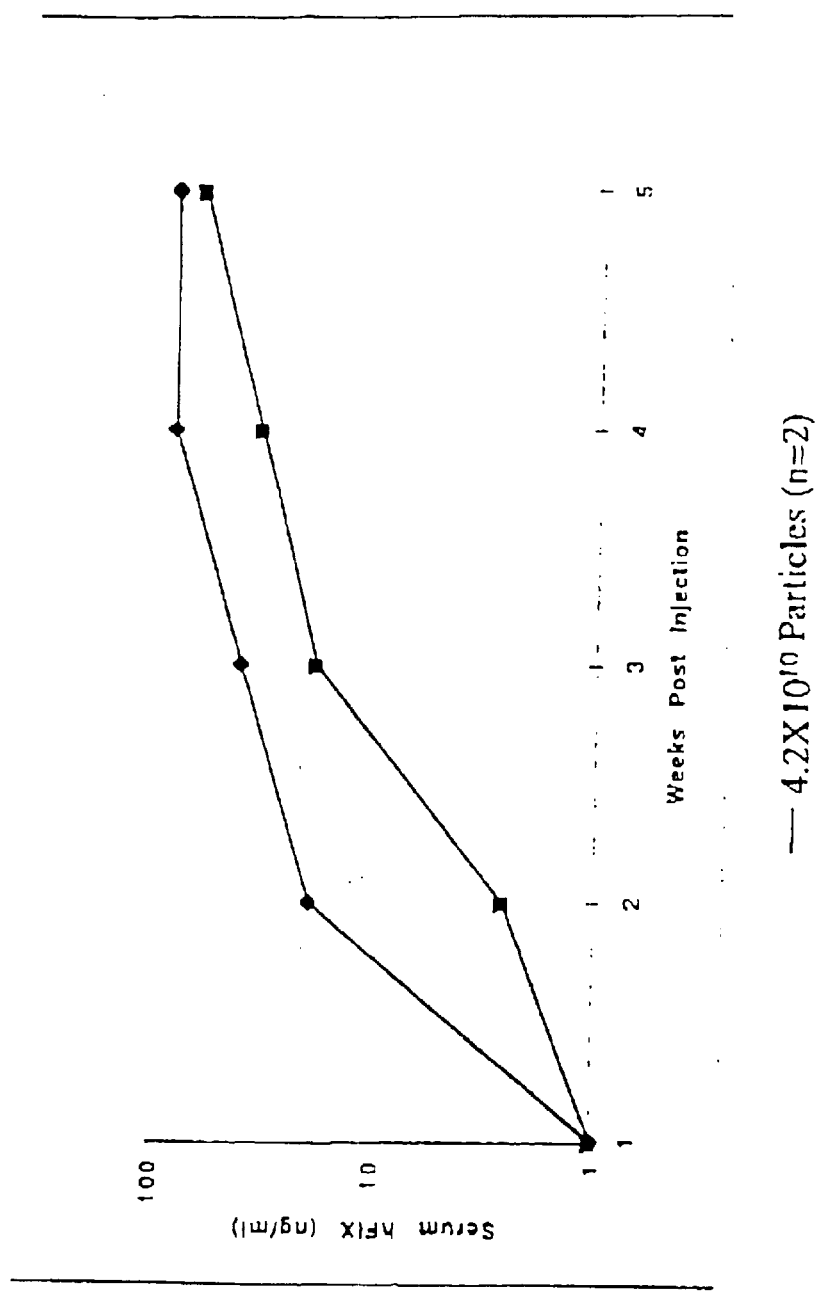
FIG. 9 is a graph showing expression of human Factor IX in immunocompromised mice that were injected intraportally with $4.2 \times 10^{10}$ particles of rAAV-MFG-hFactor IX.
Figure 10:
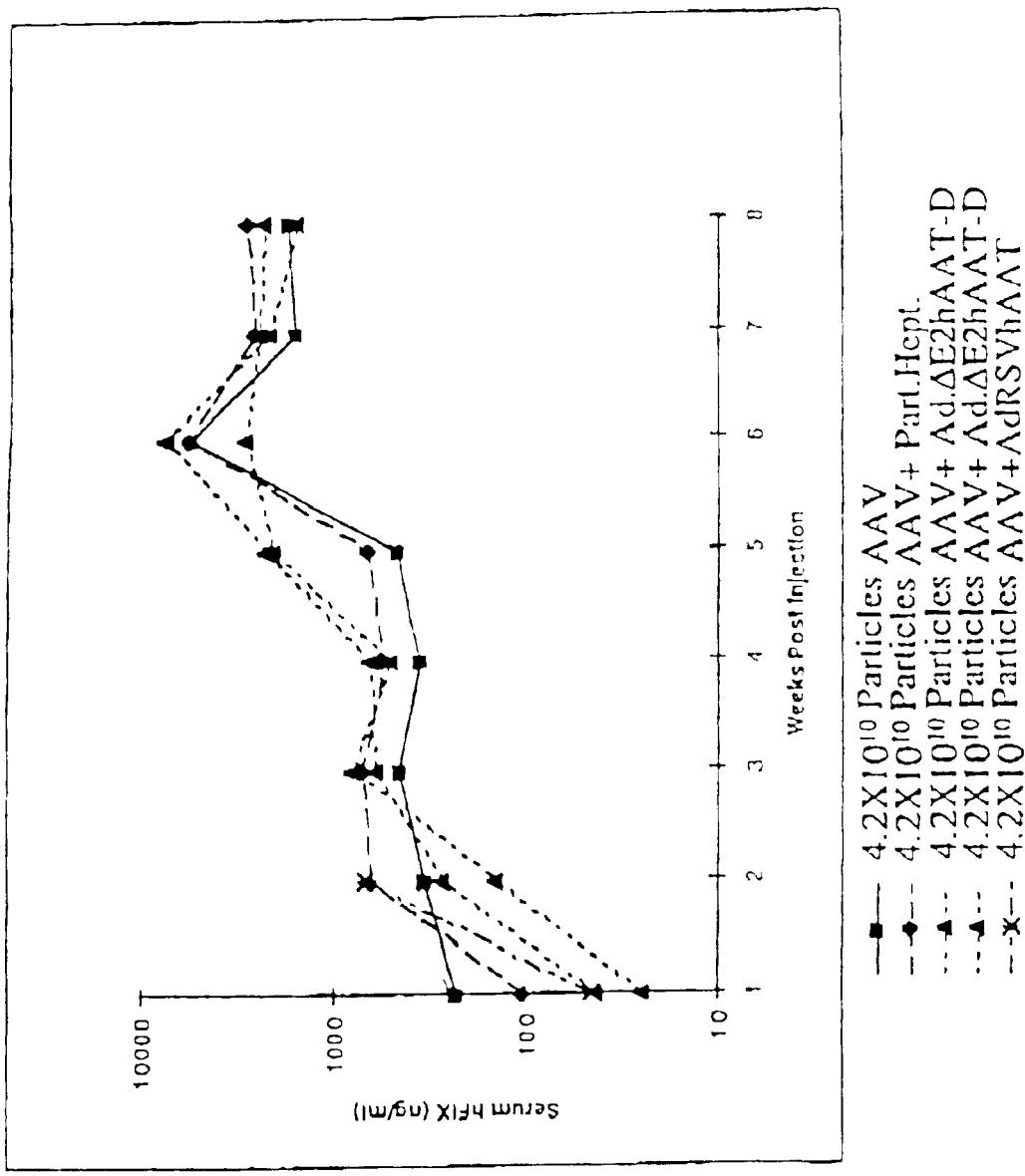
FIG. 10 is a graph showing expression of human Factor IX in immunocompetent mice that were injected intraportally with $4.2 \times 10^{10}$ particles of rAAV-MFG-hFactor IX in combination with additional treatments.

Factor IX was detectable at low levels (10–80 ng/ml) within the first week and increased continually during the first several weeks to steady state concentrations that ranged from 250 to 2000 ng/ml up at least through week 36, which was the length of the experiment. The animals administered $8.4 \times 10^{10}$ particles had somewhat higher levels of factor IX than the mice given $4.2 \times 10^{10}$ and $2.1 \times 10^{10}$ particles, however, the animals that received the two lower doses had a similar protein level. Control mice receiving no AAV or an unrelated vector (TH) had no detectable human factor IX. Similar levels of serum human factor IX were obtained in a second experiment in which immunocompetent C57BL/6 and immunodeficient C57BL/6 SCID mice (FIG. 9) were infused with $4.2 \times 10^{10}$ AAV particles. That was consistent with earlier studies suggesting factor IX was not an immunogenic protein in that immunocompetent mouse strain. (Kay et al. (1994); Barr et al., Gene Ther., 2:151–155 (1995)). In addition, anti-AAV antibodies were detected in the C57BL/6 mice but not in the C57BL/6 SCID mice 3–7 weeks following transfusion. Presence of the antibodies did not have an impact on factor IX expression.

The factor IX protein requires the post-translational addition of gamma-carboxyl groups for biologic function. To estimate the fraction of gamma-carboxylated factor IX, a calcium-dependent antibody directed against human factor IX (Bray, Weinamn & Thompson, J. Lab. Clin. Med., 107:269–278 (1986)) was used as the second antibody in an ELISA assay. From six animals, serum samples were obtained at random time points and analyzed in parallel with the calcium dependent and standard antibody (to measure total antigen).

The analysis revealed that relative to human plasma, about 90% of the recombinant human protein in the mouse serum was gamma-carboxylated, confirming that the majority of recombinant factor IX was modified post-translationally in proper fashion.

Factor IX clotting activity assays are conducted on citrated plasma samples. Combined citrated plasma from 2 normal (naive) mice had about one third of the factor IX clotting activity as normal human plasma. Addition of 1/10 volume of normal human plasma to the normal murine plasma increased the activity to 0.41 U/ml and the activity decreased to 0.33 U/ml after incubation with a murine monoclonal anti-human factor IX antibody. Thus, 0.10 U/ml of human plasma factor IX can be distinguished in murine plasma by the clotting activity assay and that the equivalent amount of added human factor IX activity was inhibited by species-specific antibody. The antibody also inhibited a comparable amount of normal human plasma factor IX added to buffer instead of normal murine plasma (from 0.07 to −0.01 U/ml).

Two distinct AAV-transduced mice showed about twice as much factor IX clotting activity as two naive mice. Activity equivalent to the amount of human factor IX antigen in the plasma from the mice was inhibited by a murine monoclonal anti-human factor IX antibody.

By immunoassay, there was no cross-reaction of murine factor IX (normal mouse plasma 0.01 U/ml) with the anti-human factor IX monoclonal. The comparable human factor IX antigen levels and amount of factor IX clotting activity that was inhibited suggests that within the limits of assay variability, the specific activity of recombinant human factor IX in the mice was normal.

In separate experiments, heparinized plasma from the same animals had citrate added, heparin was removed and factor IX clotting activities were determined with and without a polyclonal rabbit anti-human factor IX antibody. In samples from each of the same two transduced mice assayed above, the human factor IX activity was inhibited completely by the addition of the polyclonal anti-human factor IX antibody.

To determine the origin of factor IX gene expression, RNA was isolated from various organs including heart, brain, lung, liver, spleen, muscle, kidney and ovary from animals receiving $4.2 \times 10^{10}$ particles of AAV at week 7. The RNA was reverse transcribed to yield a cDNA and then amplified by PCR using primers specific for factor IX.

A strong signal was found in the liver and not in other tissues. Although it is not possible exclude low level gene expression in other tissues, the majority of hFIX mRNA was present in liver.

An rAAV encoding the human tyrosine hydroxylase cDNA (rAAV-MFG-hTH) was used to determine the transduced cell type within the liver. In the liver, the protein may be found in fibers of sympathetic innervation, but not in cells. About $1.8 \times 10^{10}$ particles of rAAV-MFG-TH vector were infused into the portal vein of mice. One, three and five weeks later, immunohistochemistry (described in greater detail hereinbelow) revealed the presence of TH protein exclusively within hepatocytes. At one week, there were rare fields with any immunostained cells. However by weeks 3 and 5, positive hepatocytes were found in most fields; multiple groups of immunostained hepatocytes were found around the portal vasculature while many of the immunostained cells were scattered randomly throughout the parenchyma. The TH positive hepatocytes at three and five weeks represented a small percentage of the hepatocyte population. The low number could indicate a high level of gene expression from a relatively few transduced cells or result for elimination of some of the transduced cells by an immune response.

To further establish the percentage of transduced cells in mice receiving rAAV-hFIX, in situ hybridization (described in greater detail hereinbelow) for hFIX mRNA's in two mice at 11 weeks had about 2 to 5% positive hepatocytes in a distribution similar to that seen for the mice receiving rAAV-TH. About 5% of the $10^8$ hepatocytes in a mouse liver were assumed to express factor IX and that on average the liver contains 2 AAV genomes per diploid cell, then there are 40 genome copies per transduced cell. The alternative is that there are some cells which contain rAAV genomes that do not express transgene product.

Infusion of recombinant adenovirus vectors into the portal vasculature results in an early and more chronic pattern of low level liver injury as determined by liver enzyme elevation and inflammatory cell infiltrates (Lieber et al., J. Virol., 70:8944–8960 (1996)). Interestingly, the toxicity may not result from an immune response directed at the viral particle but rather to viral antigens whose genes are present in the vector (Lieber et al. (1996)).

To establish whether similar toxicity occurs with rAAV, 5 animals injected with $4.2 \times 10^{10}$ AAV-MFG-human factor IX particles were monitored for serum pyruvic glutamic transaminase (SGPT), a sensitive serum marker for hepatic injury. The SGPT concentrations were all in the normal range during the first nine days and similar to that found in a naive control mouse. Similarly, there was no evidence of histological infiltrates in the liver during the first week and at seven weeks after AAV administration.

Example 6

DETECTION OF FACTOR IX EXPRESSION IN IMMUNOCOMPETENT MICE BY WESTERN BLOT ANALYSIS

AAV-MFG-human Factor IX is delivered to the liver as a single intraportal administration of $4.2 \times 10^{10}$ particles in a volume of 200 microliters of Dulbecco's Modified Eagle's Medium (DMEM) to a C57BL/6 mouse. The mouse is bled at three weeks after administration. The blood sample is diluted and is subjected to Western blot analysis using human serum as a standard. The blot is probed using polyclonal antibodies to human Factor IX.

Expression of human Factor IX was observed as a protein of about 70 kb.

Example 7

FACTOR IX EXPRESSION IN IMMUNOCOMPETENT MICE USING rAAV VECTOR IN COMBINATION WITH OTHER TREATMENTS

AAV-MFG-human Factor IX is delivered to the liver as a single intraportal administration of $4.2 \times 10^{10}$ particles in a volume of 200 µl of Dulbecco's Modified Eagle's Medium (DMEM) to C57BL/6 mice. In addition to the rAAV, some mice can receive in the same administration either adenovirus Ad.DE2hAAT-D or adenovirus AdRSVhAAT (Lieber et al., J. Virol., 70:8944–8960 (1996)), or the rAAV can be administered alone to a mouse receiving a partial hepatectomy prior to infusion. Mice are bled at the indicated number of weeks after administration depicted in FIG. 5, and the blood samples are stored frozen. The expression of human Factor IX is determined by ELISA assay as in Example 4.

Example 8

MAINTENANCE OF THE rAAV VECTOR IN MOUSE LIVER

Following post intraportal infusion of the rAAV-MFG-human Factor IX, DNA can be isolated from liver and spleen from two rAAV-treated mice. DNA is also isolated from liver of a control mouse. Fifteen µg of each DNA sample is digested for 16 hours with BamHI and XbaI. The DNA then is electrophoresed through 0.8% agarose gel and transferred to nylon membrane (Hybond N$^+$, Amersham) using the suggested alkaline transfer protocol. The membrane is prehybridized and then is hybridized with a human factor IX cDNA probe at 65° C. using Rapid-Hyb buffer (Amersham). The final stringency of wash is 0.1×SSC, 0.1% SDS at 80° C. The probe is a 810 bp human factor IX cDNA probe obtained by amplifying the DNA fragment by PCR and labelling to a specific activity of $10^8$ cpm/υg with [α-32P] dCTP using a random primer labeling kit (BRL).

Example 9

EXPRESSION OF HUMAN FACTOR IX IN MICE

At various intervals, for example 6–12 months, after transduction of mouse hepatocytes in vitro and delivery into the portal vasculature of the rAAV-treated mice, tissue samples are taken from the mice. Tissue samples also are taken at various intervals post-treatment from mice that have been treated via direct in vivo delivery of the rAAV vector virus particles into the portal vasculature. Samples are taken of the liver, spleen, brain, epithelium and other tissues. RNA then is isolated from the tissue samples and Northern blots prepared according to standard techniques, see Sambrook et al., In: Molecular Cloning: A Laboratory Manual. The filters are probed with radiolabelled rAAV vectors to determine localization of expression of the transduced gene or polynucleotide.

Example 10

IMMUNOHISTOCHEMISTRY

At varying intervals after either in vivo direct delivery of rAAV vector virus particles into the portal vasculature or ex vivo treatment (transduction of resected hepatocytes with the rAAV vector virus particles followed by delivery of transduced hepatocytes back into the host animal) tissue samples are harvested by biopsy. The majority of the tissue samples are fixed, embedded, sectioned and analyzed by light and immunofluorescence microscopy for evidence of pathology.

For detection of human tyrosine hydroxylase which is used as a marker in the experiments described herein, deparaffinized formal sections were incubated in diluted (1/500) primary rabbit polyclonal antibody to tyrosine hydroxylase (Eugene Tech International, Ridgefield, N.J.

TE101). Detection of the primary antibody employed standard ABC techniques using biotinylated goat anti-rabbit as a secondary and Elite ABC horseradish peroxidase (Vector Labs, Burlingame, Calif.) according to recommendations of the manufacturer. After washing, the slides were covered with DAB substrate (with nickel chloride added) and developed for 10 minutes at 37° C. Slides were washed in distilled water and counter stained with Methyl Green. After dehydration the slides were cleared in Histoclear (National Diagnostics, Atlanta, Ga.) and mounted. Sections of human adrenal medulla were used as positive controls while normal mouse liver sham inoculated were used as negative controls. Test livers were also incubate with non-immune pooled rabbit sera instead of primary antibody to exclude background stain.

The remaining tissue samples are analyzed for cells expressing the polynucleotide in the rAAV vector by in situ hybridization. Tissue sections are hybridized with a sense rAAV vector probe, an antisense rAAV vector probe and visualized by bright and dark field microscopy. The in situ hybridization techniques are well-known in the art, see, e.g., Grossman et al., Nature Genet., 6:335–341 (1994); Chowdhury et al., Science, 254:1802–1805 (1991).

For example, in situ hybridization was applied to detect hFactor IX-mRNA expression in the rAAV-MFG-hFIX transduced liver cells. The fresh frozen sections were fixed in 3% PFA, followed by several washes in PBS and 2×SSC. The sections were then prehybridized with 0.1M triethanolamine-0.25% acetic anhydride solution to reduce the background staining, followed by washes in PBS and 2×SSC, and stepwise dehydration in ethanol (70, 80, 95, 100%). The hybridization was carried out in a humid chamber at 55° C. oven for 4 hr. The hybridization solution contained $1.5 \times 10^6$ cpm of riboprobe in 25 µl of hybridization buffer (40% formamide, 4×SSC, 1 mg/ml tRNA, 1 mg/ml sonicated salmon sperm DNA, 4% dextran sulfate, 10 mM DTT and 5×Denhardt's solution).

The riboprobe was synthesized from a plasmid containing a 417 base pair EcoRV-EcoRV fragment of the human Factor IX cDNA which was inserted into EcoRV site of PBKS (Stratagene). The following procedure was used to synthesize both the antisense and sense probes: First, the circular plasmid was cut with BssHII to drop out the hFIX fragment flanked by both the T7 and T3 promoters. The riboprobes were then synthesized by mixing the following components in a reaction volume of 20 µl: 1×Transcription buffer; 10 mM DTT; 1 µl RNasin; 500 µM each of GTP, ATP, CTP [Promega Gemini System II]; 2 µg of linearized DNA template; 70 µCi $^{135}$S-UTP (S.A.>1.100 Ci/mmol, Amersham); and 5 units RNA polymerase (T3 for antisense, T7 for sense). The mixtures were incubated for 1 hr at 37° C., followed by the purification of the RNA probe by phenol extraction and ethanol precipitation.

The posthybridization washes were performed using 50% formamide and 2×SSC at 52° C., followed by RNAse treatment at 37° C., and several washes in 2×SSC. Finally the sections were dehydrated stepwise in ethanol (70, 80, 95, 100%), delipidated with Xylene, air dried, dipped in photographic emulsion (KODAK) exposed at 4° C. for three weeks, developed, and counter-stained with H&E. Sections were then examined and photographed by bright field and dark field microscopy (Ziess).

For negative controls, adjacent sections of transduced tissue were hybridized with a single stranded "sense" riboprobe, or non-transduced tissue was probed with the antisense probe.

Example 11

ADDITIONAL ANIMAL STUDIES

The rAAV vectors of the invention are used for in vivo direct delivery into the portal vasculature of a mammal, such as a dog, or for ex vivo treatment, using known techniques, see, e.g., Kay et al., Proc. Natl. Acad. Sci. USA, 89:89–93 (1992); Kay et al., Science, 262:117–119 (1993). An rAAV vector comprising either Factor IX or Factor VIII is used for in vivo and ex vivo treatment of both normal and hemophiliac dogs.

All references mentioned in the instant specification are herein incorporated by reference.

The invention now being fully described, it will be apparent to one of ordinary skill in the art that many changes and modifications can be made thereto without departing from the spirit or scope of the appended claims.

What is claimed is:

1. A method for treating hemophilia B in a mammal, comprising:

administering recombinant adeno-associated virus (rAAV) particles to a mammalian liver cell, wherein said rAAV particles consist essentially of AAV terminal repeats flanking a MFG promoter, adjacent MLV intervening sequence including the splice donor and acceptor sites and env ATG, a polynucleotide encoding Factor IX operably linked to said MFG promoter, and a bovine growth hormone polyA sequence, wherein following infection of said mammalian cells, Factor IX protein is expressed in the liver.

2. The method of claim 1, wherein said Factor IX protein is diffusible and is delivered to the circulating blood.

3. The method of claim 1, wherein said administering comprises injecting said rAAV into the portal vasculature of said mammal.

4. The method of claim 1, wherein said administering comprises injecting said rAAV intravenously into said mammal.

5. A pharmaceutical composition for treating a hemophilia B comprising, (a) recombinant adeno-associated virus (rAAV) particles consisting essentially of AAV terminal repeats flanking a MEG promoter, adjacent MLV intervening sequence including the splice donor and acceptor sites and env ATG, a polynucleotide encoding Factor IX operably linked to the MPG promoter, a bovine growth hormone polyA sequence, and (b) a pharmaceutically acceptable carrier.

* * * * *